United States Patent [19]
Siiman et al.

[11] Patent Number: 5,994,089
[45] Date of Patent: *Nov. 30, 1999

[54] SIMULTANEOUS ANALYSES OF WHITE BLOOD CELL SUBSETS USING MULTI-COLOR, MULTI-INTENSITY FLUORESCENT MARKERS IN FLOW CYTOMETRY

[75] Inventors: Olavi Siiman, Davie; Alexander Burshteyn, Hialeah; Julie Wilkinson, Weston; Ravindra Mylvaganam, Hollywood, all of Fla.

[73] Assignee: Coulter International Corp., Miami, Fla.

[*] Notice: This patent is subject to a terminal disclaimer.

[21] Appl. No.: 08/976,031

[22] Filed: Nov. 21, 1997

Related U.S. Application Data

[63] Continuation-in-part of application No. 08/857,941, May 16, 1997, Pat. No. 5,891,741.

[51] Int. Cl.$^6$ .................................................. G01N 33/548
[52] U.S. Cl. .......................... 435/7.24; 436/512; 436/513; 436/529; 436/800; 530/391.1; 530/391.3; 530/391.5
[58] Field of Search .............................. 530/391.1, 391.3, 530/391.5; 435/7.24; 436/512, 513, 529, 800

[56] References Cited

U.S. PATENT DOCUMENTS

| | | | |
|---|---|---|---|
| 4,499,052 | 2/1985 | Fulwylen | 422/52 |
| 5,206,143 | 4/1993 | Horan et al. | 435/7.24 |
| 5,527,713 | 6/1996 | Bolton et al. | 436/529 |
| 5,538,855 | 7/1996 | Orfao de Matos | 435/7.24 |
| 5,658,741 | 8/1997 | Bolton et al. | 435/7.2 |

FOREIGN PATENT DOCUMENTS 594772  8/1996  European Pat. Off. .

OTHER PUBLICATIONS

H. Shapiro, in Practical Flow Cytometry, 3$^{rd}$ ed., Chap. 7, p. 291, Wiley–Liss, Inc., New York, NY (1995) [Shapiro I].
A. Beavis et al, Cytometry, 15:371–376 (1994).
M. O'Brien et al, Cytometry, 21:76–83 (1995).
M. Roederer et al, Cytometry, 21:187–196 (1995) [Roederer I].
M. Roederer et al, Cytometry, 24:191–197 (1996) [Roederer II].
T. Ried et al, Proc. Natl. Acad. Sci. USA, 89:1388–1392 (1992).
A. Gothot et al, Cytometry, 24:214–225 (1996).
M. Roederer et al, Tissue Antigens, 48:485 (1996) [Roederer III].
A. Saunders et al, Ann. N. Y. Acad. Sci., 468:128 (1986).
H. Shapiro, in Practical Flow Cytometry, 1$^{st}$ ed., pp. 127–128, Alan R. Liss, Inc. (1985) [Shapiro II].
P. Horan et al, Proc. Natl. Acad. Sci. USA, 83:8361–8365 (1986).
C–M. Liu et al, Am. J. Clin. Path., 92:721–728 (1989).
P. Carayon et al, J. Immunol. Methods, 138:257–264 (1991).
U.S. Application No. 08/857,941, filed May 16, 1997.

Primary Examiner—Christopher L. Chin
Attorney, Agent, or Firm—Mary E. Bak; Warren W. Kurz

[57] ABSTRACT

A method for a single-measurement quantification of multiple populations of white blood cells (WBC) is based upon the labeling of different pairs of cell populations, each pair containing mutually exclusive cell receptors which are expressed at substantially similar receptor densities with labeled ligands for each receptor. One cell population is labeled with a ligand capable of binding to a first cell surface receptor which ligand is directly conjugated to a fluorescent phycobiliprotein or tandem dye; and a second cell population is labeled with a ligand capable of binding to a second cell surface receptor, which ligand is cross-linked by an aminodextran to a fluorescent phycobiliprotein or tandem dye. The phycobiliproteins upon laser excitation produce a different detectable fluorescence intensity for each cell population. Use of such pairs of conjugates enable two populations of cells with similar receptor densities to be distinguished with the use of a single color marker. Further use of additional ligands to other cell surface receptors and additional phycobiliprotein or tandem dye, or other markers in the same manner, enables the simultaneous quantification of up to 45 different cell populations with one laser line and four fluorescent colors.

5 Claims, 16 Drawing Sheets

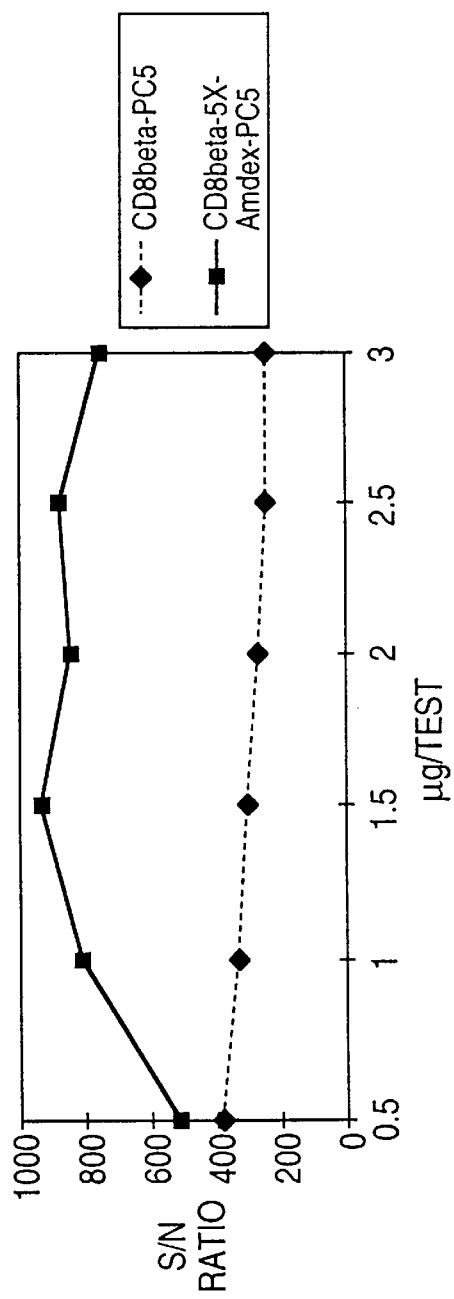
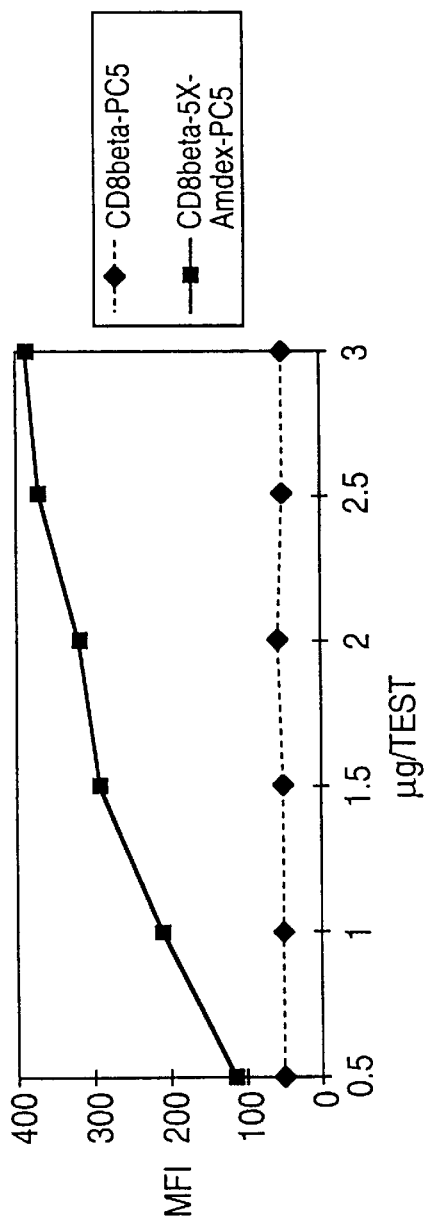

FIG. 5A
| μg/TEST | S/N | | MFI-POS | | MFI RATIO |
|---|---|---|---|---|---|
| | CD4-ECD | CD4-5X-Amdex-ECD | CD4-ECD | CD4-5X-Amdex-ECD | |
| 0.015 | 99 | 239 | 18 | 267 | 5.3 |
| 0.03 | 158 | 213 | 29 | 349 | 7.0 |
| 0.06 | 211 | 169 | 41 | 359 | 7.2 |
| 0.125 | 237 | 102 | 47 | 359 | 7.2 |
| 0.25 | 245 | 90 | 50 | 398 | 8.0 |
| 0.5 | 248 | 52 | 53 | 485 | 9.7 |
FIG. 5B
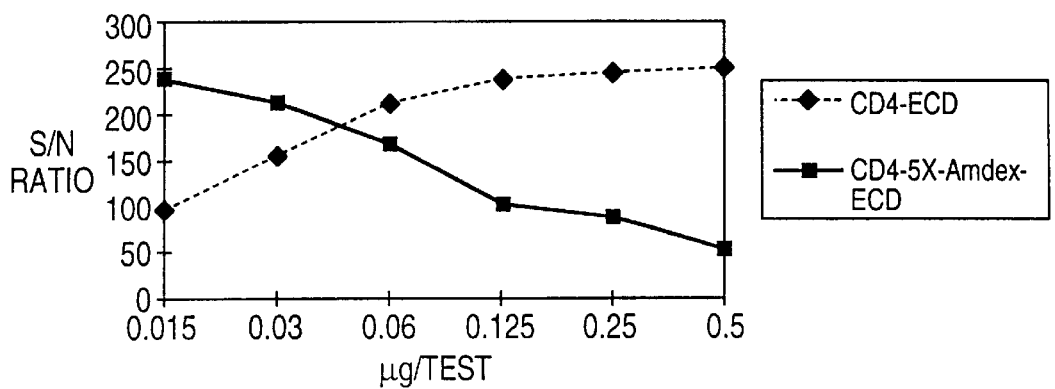
FIG. 5C
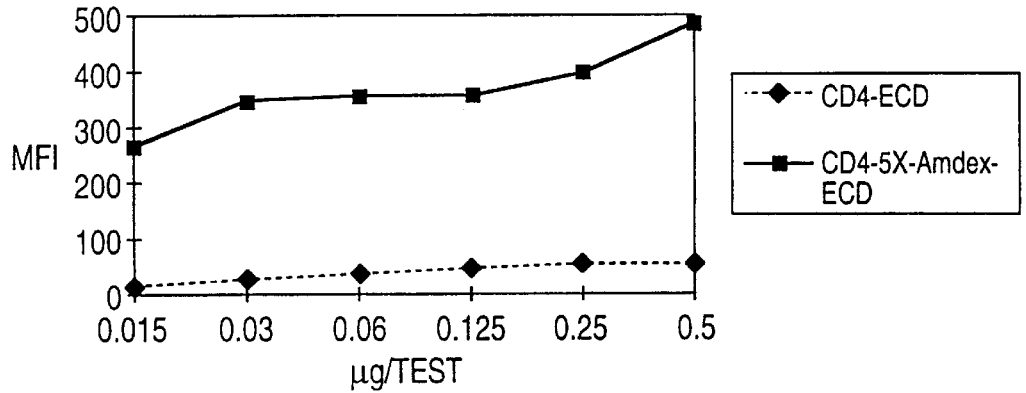

CD56-PE, CD4-5X-Amdex-PE

CD4-PE, CD56-PE

CD8αβ-PE, CD4-5X-Amdex-PE

CD4-PE, CD8αβ-PE

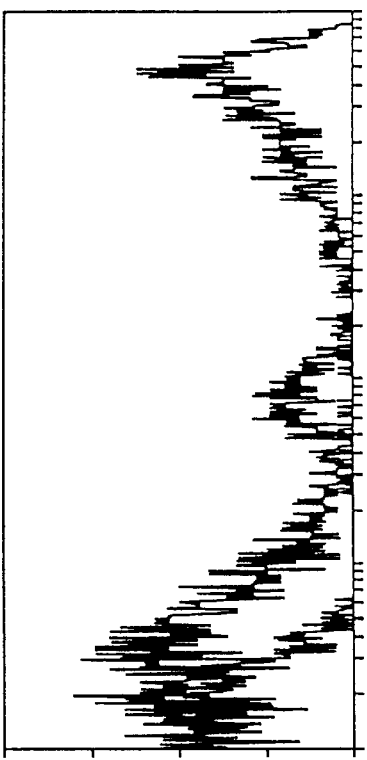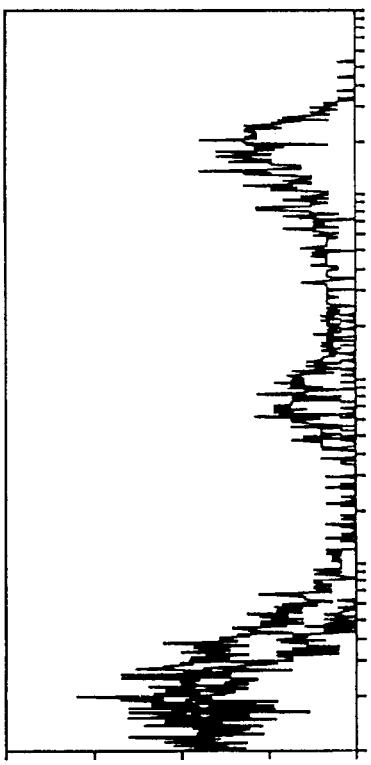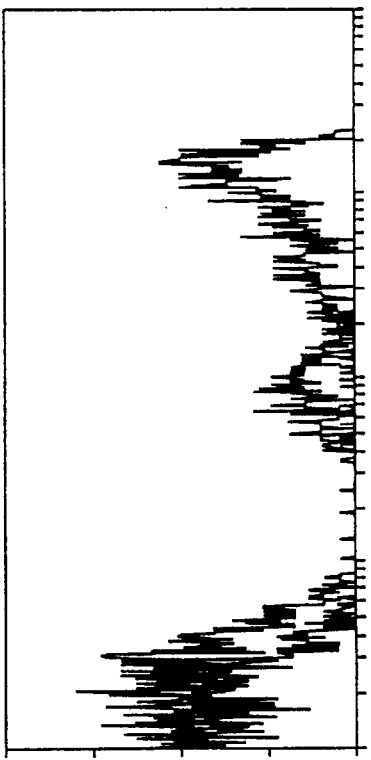

SIMULTANEOUS ANALYSES OF WHITE BLOOD CELL SUBSETS USING MULTI-COLOR, MULTI-INTENSITY FLUORESCENT MARKERS IN FLOW CYTOMETRY

CROSS-REFERENCE TO OTHER INVENTIONS

This is a continuation-in-part application of U.S. patent application Ser. No. 08/857,941, filed May 16, 1997 now U.S. Pat. No. 5,891,741.

FIELD OF THE INVENTION

The present invention relates to methods for analyses of cell populations using fluorescent labels or markers. More specifically, the method employs a combination of such markers directly bound to a ligand for an appropriate cell surface receptor and such markers conjugated via an aminodextran to a ligand for a second cell surface receptor. Differences in fluorescent signals emitted by the different types of ligand-conjugated markers expand the number of cell subsets that can be detected at any one time.

BACKGROUND OF THE INVENTION

Multiplex labeling of cells for analysis of mixed cell populations by flow cytometry has progressed in various ways. Only a finite number of fluorescence emission colors of known organic fluorophores can be squeezed into the visible-near-UV-near-IR spectral regions in which flow cytometry measurements are made. The limitations have been dictated by the bandwidths of emission bands, the spectral overlap between these emission bands, and the excitation wavelength requirements. Up to eight colors requiring three laser lines have been introduced in various stages: two- to four-color [H. M. Shapiro in PRACTICAL FLOW CYTOMETRY, 3rd ed., Wiley-Liss, Inc., New York, N.Y., 1995, Chap. 7, p. 291]; five color [A. J. Beavis and K. J. Pennline, Cytometry, 15: 371–376 (1994); M. C. O'Brien et al, Cytometry, 21:76–83 (1995); M. Roederer et al, Cytometry, 21: 187–196 (1995)]; six color [M. Roederer et al, Cytometry, 24: 191–197 (1996)]; seven color for imaging [T. Ried et al, Proc. Natl. Acad. Sci. USA, 89: 1388–1392 (1992); A. Gothot et al, Cytometry, 24: 214–225 (1996)]; and eight color [M. Roederer et al, Tissue Antigens, 48: 485 (1996), abstract TC-6-02]. The six and seven color cases appear to represent the present upper limit for flow cytometry applications in which known organic dyes are used as fluorescent labels, since the eight-color example cannot as yet be considered to be of clinical significance due to severe overlap between emission bands of the fluorochromes.

As the upper limit in the number of usable colors was reached, other methods, based on fluorescence intensity differences, either intrinsic to analyzed cell populations or contrived by various means, have been described. Mutually exclusive pairs of targeted white blood cell populations with widely different, intrinsic numbers of receptors per cell can be labeled by a single color marker and analyzed by flow cytometry [U.S. Pat. No. 5,538,855, issued Jul. 23, 1996]. U.S. Pat. No. 4,499,052, issued Feb. 12, 1985 describes a method of distinguishing multiple subpopulations of cells by labeling specific antibodies with fluorescent polymers containing different, pre-selected ratios of fluorescein and rhodamine [see also, A. M. Saunders and C.-H. Chang, Ann. N. Y. Acad. Sci., 468:128 (1986)]. H. M. Shapiro in PRACTICAL FLOW CYTOMETRY, 1st ed., Alan R. Liss, Inc., pp. 127–128 (1985) describes a method using three different antibodies labeled with fluorochrome A, B, and a combination of A and B. U.S. Pat. No. 5,206,143, issued Apr. 27, 1993 describes saturated and sub-saturated amounts of marker mixed with the sample of cells. Quantitative differences in fluorescence intensity of one or two fluorochromes used for labeling cells were obtained. Each subset to be analyzed was labeled with a different amount of fluorochrome, exhibiting fluorescence intensities within a distinguishable range. Mixtures of fluorescein- and phycoerythrin-labeled and unlabeled antibodies were used to produce fluorescence intensity differences of several orders of magnitude among various cell subsets [P. K. Horan et al, Proc. Natl. Acad. Sci. USA, 83: 8361–8365 (1986)]. Use of this method to identify helper and suppressor/cytotoxic T cells, NK and B cells, and monocytes in whole blood was shown [C.-M. Liu et al, Am. J. Clin. Path, 92: 721–728 (1989)]. Further, eight leukocyte subsets in whole blood were analyzed with six monoclonal antibodies linked with one of three fluorochromes [P. Carayon et al, J. Immunol. Methods, 138: 257–264 (1991)].

Enhanced phycoerythrin (PE, excitation, 486–575 nm, emission, 568–590 nm) fluorescence intensities per marker for direct antibody-PE conjugates were obtained by substituting the direct conjugates with aminodextran-crosslinked conjugates, prepared by methods that are described in ANTIBODY-AMINODEXTRAN-PHYCOBILIPROTEIN CONJUGATES, parent U.S. patent application Ser. No. 08/847,941 filed May 16, 1997, and incorporated by reference herein. In this parent U.S. patent application, crosslinked conjugates were loaded with substantially more PE than the direct 1:1 antibody-PE conjugates by simultaneously reacting iminothiolane-activated antibody and PE with sulfo-SMCC-activated aminodextran in appropriate molar ratios. Thus, use of these loaded conjugates in saturation amounts in analysis of cell subsets in biological samples resulted in amplification of the PE fluorescence signals from individually-marked cells by a factor of two- to twenty-fold over the PE fluorescence intensity from cells marked with direct antibody-PE conjugates. The amplification of fluorescence was initially demonstrated for marked cells which usually showed dim fluorescence intensity when their receptors were saturated with direct antibody-PE conjugates. Other types of antibody-aminodextran conjugates are described in U.S. Pat. No. 5,527,713 issued Jun. 18, 1996; and U.S. Pat. No. 5,658,741 issued Aug. 19, 1997; see also, European Patent No. 0 594 772 B1.

There remains a need in the art for simple methods to permit greater numbers of cell populations to be distinguished by fluorescent markers.

SUMMARY OF THE INVENTION

In one aspect, the invention provides a method for a single-measurement quantification of multiple populations of white blood cells (WBC) based upon the labeling of different pairs of cell populations. Each cell population of the pair contains mutually exclusive cell receptors which are expressed at substantially similar receptor densities on each cell population of the pair. One cell population is labeled with a ligand capable of binding to a first cell surface receptor, which ligand is directly conjugated to a fluorescent phycobiliprotein. A second cell population is labeled with a ligand capable of binding to a second cell surface receptor, which ligand is cross-linked to an aminodextran which is conjugated to the fluorescent phycobiliprotein. Upon laser excitation, the directly labeled ligands bound to the first receptor produce a different detectable fluorescence intensity than the labeled cross-linked ligands bound to the second receptor. Use of such pairs of ligands enable two populations of cells with similar receptor densities to be distinguished with the use of a single color marker.

In another aspect, the invention provides a method for a single-measurement quantification of multiple populations of white blood cells (WBC) based upon the labeling of different pairs of cell populations, each pair containing mutually exclusive cell receptors which are expressed at substantially similar receptor densities. For each first population of cells in a pair of cell populations, a different first ligand is labeled directly with a different phycobiliprotein. For each second population of cells in a pair, a second ligand which differs from the first ligand of the pair forms a conjugate by cross-linking to an aminodextran, and being labeled with the phycobiliprotein. Within each pair of first and second ligands, the phycobiliproteins are the same; however, each separate pair of cell populations uses a different color phycobiliprotein (or a phycobiliprotein excited by a different laser excitation line) to label its first and second ligands. Following incubation of a biological sample containing one or more pairs of cell populations with each pair of first and second labeled ligands for a time sufficient to permit receptor-labeled ligand complexes to form therebetween, the sample is subjected to a laser excitation line to cause the labels to fluoresce. The intensities of fluorescent emissions of each first cell population bound to each labeled first ligand and the fluorescent emissions of each second population bound to each labeled second ligand are measured using flow cytometry. By this method, the cell populations may be distinguished by detectably different intensity and color signals. This method can be optionally modified by the use of labels which produce fluorescent emissions that do not overlap with the phycobiliproteins used (i.e., labels which are generally proteinaceous or small molecules which emit below 550 nm, such as FITC). Thus, this method permits up to seven markers to be employed in a single quantitation measurement using a single laser, four color flow cytometer.

In still another aspect, the method is employed to distinguish between four cell populations using two single color phycobiliproteins. In a further aspect, the method is employed to distinguish between six cell populations using three single color phycobiliproteins. A fourth color, such as FITC, may be added to bring the total number of markers used in the method to seven.

In yet a further aspect, the method involves the use of two laser excitation lines, thereby permitting a maximum of twelve different signals having different color and intensity characteristics, enabling the identification of twelve different cell populations in a method which does not rely on substantial differences between the densities of the cell surface receptors, but only on the use of mutually exclusive cell surface receptors for each pair of cell populations to be identified.

In yet a further aspect, the present invention provides an antibody-aminodextran-tandem dye-conjugate, which conjugate contains two to twenty tandem dye molecules per amino dextran molecule, wherein said aminodextran has a degree of substitution with 1,3-diaminopropane of 1/40–1/8. Also included as an aspect of this invention are methods of making and using such antibody-aminodextran-tandem dye conjugates.

Other aspects and advantages of the present invention are described further in the following detailed description of the preferred embodiments thereof.

BRIEF DESCRIPTION OF THE DRAWINGS

FIG. 4A is a graph plotting signal-to-noise ratio (S/N) for CD8αβ-PC5 ligand (diamond) vs. CD8αβ-5X-Amdex-PC5 ligand (square) for trial 1, fraction 42 of Example 7 below.

FIG. 4B is a graph plotting positive mean channel intensity for CD8αβ-PC5 ligand (diamond) vs. CD8αβ-5X-Amdex-PC5 ligand (square) for trial 1, fraction 42 of Example 7 below.

FIG. 5A is a tabular report of the S/N, positive mean fluorescence and MFI ratio for the direct CD4-ECD ligand and a single pooled sample of CD4-5X-Amdex-ECD conjugates from trial 2 of Example 8. These were titered with two-fold serial dilutions, starting at 0.5 μg (based on ELISA analysis for CD4-5X-Amdex-ECD and $A_{280}$ value for CD4-ECD) per tube.

FIG. 5B is a graph plotting the S/N ratio vs. microgram/test of the results of FIG. 5A.

FIG. 5C is a graph plotting MFI vs. microgram/test of the results of FIG. 5A.

FIG. 11A is a histogram similar to that of FIG. 10A using markers CD19-PC5 and CD8αβ-5X-Amdex-PC5.

FIG. 11B is a histogram similar to that of FIG. 11A, but obtained with a different titer of the CD8αβ-5X-Amdex-PC5 marker to show optimum separation between the position of the positive and negative count versus intensity distributions.

FIG. 11C is a histogram similar to that of FIG. 10C using markers CD8αβ-PC5 and CD19-PC5.

FIG. 15A is a histogram showing dual color, four markers CD56-PE/CD4-5X-Amdex-PE and CD19-PC5/CD8αβ-5X-Amdex-PC5, for Q-PREPed and washed samples run with 488.0 nm Ar+ laser excitation on the Coulter XL flow cytometer.

FIG. 15B is a histogram of the same experiment showing use of two additional color markers, CD3-ECD and CD45RO-FITC mixed with whole blood already containing the other markers.

FIG. 15C is a histogram of the same experiment showing the detection of fluorescence for CD3-ECD vs. CD56-PE and CD4-5X-Amdex-PE.

FIG. 15D is a histogram of the same experiment showing the detection of fluorescence for CD3-ECD vs. CD19-PC5 and CD8αβ-5X-Amdex-PC5.

DETAILED DESCRIPTION OF THE INVENTION

Figure 1A:
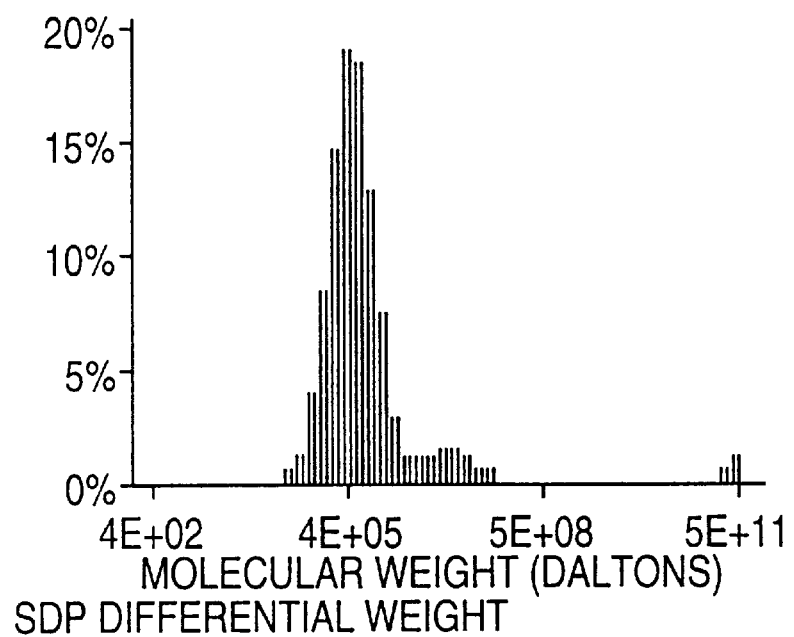
FIG. 1A is a histogram showing a plot of relative weight percent (mass %) of aminodextran molecules (vertical axis) versus their molecular weights (daltons) or size distribution processor (SDP) differential weight distribution of a 5X-aminodextran (5X-Amdex) sample suitable for use in preparation of antibody-5X-Amdex-phycobiliprotein (i.e., PE, PC5, or ECD) conjugates which yield enhanced fluorescence emission intensities, before sulfosuccinimidyl 4-[N-maleimidomethyl]cyclohexane-1-carboxylate (sulfo-SMCC) activation and purification as measured on a Coulter N4MD Sub-Micron Particle Analyzer.

The present invention provides an improved method of quantifying multiple subsets of white blood cell populations by combining several types of "markers" for use in flow cytometry. Specifically, a method for a single-measurement quantification of multiple populations of white blood cells (WBC) having substantially similar cell surface receptor densities may occur in a flow cytometric analysis by using the following steps. One cell population which is characterized by a particular cell surface receptor which is not present on a second cell population is incubated with a ligand (preferably an antibody) capable of binding to the cell surface receptor. This ligand is conventionally, directly conjugated to a fluorescent phycobiliprotein. A second cell population which is characterized by the presence of a second cell surface receptor which is different from the receptor on the first cell population and not found on the first cell population is incubated with a ligand capable of binding to this cell surface receptor and not the first cell surface receptor. This second ligand is preferably an antibody cross-linked to the same fluorescent phycobiliprotein through an aminodextran carrier. Upon excitation by a laser, the phycobiliprotein produces a different detectable fluorescence intensity for each cell population, due to the differences between its direct conjugation to the ligand binding the first cell surface receptor and its cross-linked conjugation to the ligand binding the second cell surface receptor. Thus a single color phycobiliprotein may distinguish between two cell populations based on differences in fluorescent intensity.

To facilitate understanding of the method of this invention, the following descriptions of the components used in this method are described as follows.

A. Ligands

As used herein the term "ligand" refers to a component which preferentially binds to all or a portion of a cell surface receptor. Preferably, a ligand useful in this invention is an antibody or a functional fragment thereof capable of binding to a cell surface receptor on a WBC population. Such antibodies or fragments may be defined to include polyclonal antibodies from any native source, and native or recombinant monoclonal antibodies of classes IgG, IgM, IgA, IgD, and IgE, hybrid derivatives, and fragments of antibodies including Fab, Fab' and F(ab')2, humanized or human antibodies, recombinant or synthetic constructs containing the complementarity determining regions of an antibody, and the like. The methods useful for construction of all such ligands are known to those of skill in the art. All such ligands are characterized by the desired ability to bind the specified cell surface receptor on a population of white blood cells.

As an example, monoclonal antibodies used in the examples of this invention were generally obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, Nature, 256: 495–497 (1975), which teaching is incorporated herein by reference. Of course, the particular method of making and the type of monoclonal antibody is not limited to such techniques and it is envisioned that any technique for making such antibodies is within the practice of the invention. Any ligand which can target receptor sites on, or in, cells may be used, since the amplification of fluorescent intensities using the antibody-dextran-phycobiliprotein conjugate does not depend on the density of the particular receptor sites on a cell. Thus, the selection of the ligand or antibody is not a limiting factor in this invention.

B. Markers: Phycobiliproteins or Biliproteins, Tandem Dyes and Others

The term "markers" generally refers to molecules, preferably proteinaceous, but also small chemical molecules, which enable detection by emitting a detectable signal of a particular wavelength upon excitation by a laser. Phycobiliproteins, tandem dyes, certain fluorescent proteins, small chemical molecules, and certain molecules detectable by other means can all be considered markers for flow cytometry analyses. See, e.g., the markers listed in Handbook of Fluorescent Probes and Research Chemicals, 6th Ed., R. P. Haugland, Molecular Probes, Inc., Eugene, Oreg. (1996). Throughout this specification, the term "markers" may also be used to refer to the conjugates formed by the ligand which is directly labeled with a particular marker, e.g., CD56-PE, or the conjugates formed by the ligand which is cross-linked to a particular marker through an aminodextran, e.g., CD56-5X Amdex-PE. The term will be clear from the context of this application.

"Phycobiliproteins" are a family of macromolecules found in red algae and blue-green algae. The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons. The biliproteins will normally be comprised of from 2 to 3 different subunits, where the subunits may range from about 10,000 to about 60,000 molecular weight. The biliproteins are normally employed as obtained in their natural form from a wide variety of algae and cyanobacteria.

The presence of the protein in the biliproteins provides a wide range of functional groups for conjugation to proteinaceous and non-proteinaceous molecules. Functional groups which are present include amino, thiol, and carboxyl. In some instances, it may be desirable to introduce functional groups, particularly thiol groups when the biliprotein is to be conjugated to another protein. Each phycobiliprotein molecule contains a large number of chromophores. An antibody molecule directly labeled with fluorescein will have between 1 and 3 chromophores associated with it. An antibody molecule directly labeled by conjugation with a phycobiliprotein may have as many as 34 associated chromophores, each with an absorbance and quantum yield roughly comparable to those of fluorescein.

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and found in M. C. Custer and M. T. Lotze, *J. Immunol. Methods*, 128, 109–117 (1990), to be the only tested fluorophore that produced adequate signal.

The tandem dyes are non-naturally occurring molecules which may be formed of a phycobiliprotein and another dye. See, for example, U.S. Pat. No. 4,542,104 issued Sep. 17, 1985 and U.S. Pat. No. 5,272,257 issued Dec. 21, 1993, incorporated by reference herein. Examples of tandem dyes useful in the present invention are phycoerythrocyanin or PC5 (PE-Cy5, phycoerythrin-cyanin 5.1; excitation, 486–580 nm, emission, 660–680 nm) [A. S. Waggoner et al, *Ann. N.Y. Acad. Sci.*, 677:185–193 (1993) and U.S. Pat. No. 5,171,846 issued Dec. 15, 1992, incorporated by reference herein] and ECD (phycoerythrin-texas red; excitation, 486–575 nm, emission, 610–635 nm). Other known tandem dyes are PE-Cy7, APC-Cy5, and APC-Cy7 [M. Roederer et al, *Cytometry*, 24:191–197 (1996)]. Since tandem dyes, PC5 and ECD, have been successfully directly conjugated to monoclonal antibodies by several methods which involve iminothiolane activation of the dye, the procedures are anticipated to be transferable to preparation of aminodextran-crosslinked antibody-tandem dye conjugates as described herein.

Still other markers which may be directly conjugated to a ligand and used with the phycobiliproteins or tandem dyes in this invention to add additional numbers of markers (labeled ligands) to the method include small molecules which upon excitation emit wavelengths of less than 550 nm. Such molecules do not overlap with the emissions of the phycobiliproteins. One example of such a marker is fluorescein isothiocyanate (FITC). Others are listed in the Handbook cited above.

Still other markers which may be employed in this method to provide additional colors are the proteins known as the green fluorescent proteins and blue fluorescent proteins; also useful may be markers which emit upon excitation by ultraviolet light.

The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained commercially from known sources.

C. Ligand-Aminodextran-(Phycobiliprotein or Tandem Dye) Conjugates

The conjugates of the present invention are dextran crosslinked, ligand-(phycobiliprotein or tandem dye) conjugates containing up to twenty five phycobiliprotein or tandem dye molecules per dextran molecule. These conjugates are advantageous in that they are able to produce an amplification of fluorescence intensity over direct antibody-phycobiliprotein labeled cells of two fold or greater. Preferably, the dextran component of these conjugates is aminodextran. Preferably the cross-linked aminodextran-(phycobiliprotein or tandem dye) conjugate contains two to twenty phycobiliproteins or tandem dye molecules per aminodextran molecule, wherein said aminodextran has a degree of substitution with 1,3-diaminopropane of $\frac{1}{40}$ to $\frac{1}{7}$. These conjugates are advantageous in that they are able to produce an amplification of fluorescence intensity over direct antibody-phycobiliprotein conjugates.

Aminodextrans can be prepared by methods described in U.S. Pat. No. 5,466,609 issued Nov. 14, 1995 and U.S. Pat. No. 5,527,713 issued Jun. 18, 1996, by periodate oxidation of dextran followed by reaction with 1,3-propanediamine, which teaching are incorporated herein by reference. Of course, the particular method of making the aminodextrans is not limited to such techniques and it is envisioned that any technique for making such aminodextrans is well within the knowledge of those of skill in the art. Preferably, the aminodextran is 5X-Amdex and 1X-Amdex, most preferably the aminodextran is 5X-Amdex. The preferred aminodextran has a degree of substitution with 1,3-diaminopropane of $\frac{1}{7}$ or less, but not less than $\frac{1}{40}$, which is the degree of substitution for 1X-Amdex.

In the conjugate, the number of biliproteins or tandem dye molecules per dextran will depend upon concentrations of activated species during conjugation, degree of activation of species, size and shape of dextran derivative, and size and shape of biliprotein or tandem dye. A number of linking groups may be employed for conjugating the biliprotein or tandem dye to the dextran. There is ample literature for conjugating phycobiliprotein to proteins. The same methods may be employed where the tandem dye is used in place of the phycobiliprotein in this invention. See for example, the description of which are incorporated by reference herein. Examples of commercially available cross-linking reagents are disclosed in the Pierce Catalog and Handbook, Life Science and Analytical Research Products, Pierce Chemical Company, Rockford, Ill., 1994/1995. Known linking procedures as described in the above publications may be employed. For example, the phycobiliprotein may be activated with 2-iminothiolane to introduce more thiol groups and conjugated to sulfo-SMCC-activated aminodextran.

The protein-aminodextran conjugates useful in this invention were prepared as described in U.S. Pat. No. 5,527,713, incorporated herein by reference, except that two different proteins, one a monoclonal antibody and the other a fluorescent protein (PE) were conjugated simultaneously to the aminodextran (also known as "Amdex"). Preferably, conjugation of antibody and phycobiliprotein to aminodextran is accomplished by activation of PE, activation of antibody, and activation of aminodextran as described in detail in Example 1 below.

D. Methods of the Present Invention

The conjugates may be used in a wide variety of ways. For example, for enhancing known methodologies for the detection, diagnosis, measurement and study of antigens, either present as individual molecules or in more complex organizations, such as viruses, cells, tissue, organelles, e.g., plasmids, nuclei, etc. The conjugates may be used in immunoassays or competitive protein binding assays, where the biliproteins or tandem dyes serve as fluorescent labels.

According to the present invention, a desirable use of the subject conjugates is fluorescent staining of cells. These conjugates may be used as single markers which provide an enhanced signal. The enhanced signal makes the conjugates of the invention particularly desirable for detecting non-abundant antigenic sites on cells (e.g., cells having between 10–1000 antigenic receptor sites, which would normally show fluorescence intensities close to or obscured by background fluorescence). For example, cells stained with these conjugate markers may then be observed under a microscope, the presence of the fluorescer being diagnostic of the presence of a specific determinant site or the cells may be detected in a fluorescence activated cell sorter (FACS).

In another embodiment the conjugates may be used in combinations, where the fluorescence emission maximum of the biliproteins and tandem dyes are separated by at least about 15 nm, preferably by at least about 25 nm. Alternatively, the biliprotein or tandem dye conjugates may be used in conjunction with other protein or non-protein fluorescers, where the emission maxima are separated by at least about 55 nm, preferably about 58 nm.

By using combinations of fluorescers, one can provide for the detection of subsets of aggregations, such as particular types of cells, strains of organisms, strains of viruses, the natural complexing or interaction of different proteins or antigens, etc. In some embodiments, combinations include fluorescein with biliproteins capable of being activated with the same laser light source, e.g., where the biliproteins have absorption maxima in the range of about 450–650 nm.

In a preferred embodiment, the conjugates of the present invention are used in such staining methodologies in tandem with another ligand which is directly and conventionally conjugated with a phycobiliprotein, i.e., not through cross-linking with the aminodextran. The use of these crosslinked antibody-Amdex-(phycobiliprotein or tandem dye) conjugates in this manner is not limited to ligands or antibodies for which the antigenic receptors on white blood cells are few in number, such that fluorescence signals of appropriate magnitude can then be observed above the background fluorescence of cells with the antibody-aminodextran-(phycobiliprotein or tandem dye) markers. Antibodies for which cell surface receptors exist in larger numbers, 1000 per cell and higher, can also be used in the preparation of aminodextran-crosslinked antibody-(phycobiliprotein or tandem dye) conjugates, which can be used according to this invention to further amplify fluorescence intensities of targeted cell populations.

Thus, according to this invention, cell populations may be identified by using one or more pairs of: (a) a conventional, direct antibody-(phycobiliprotein or tandem dye) conjugate prepared with an antibody which binds a cell surface antigenic receptor which is expressed on a first white cell subpopulation in about the same or fewer numbers per cell as a second cell surface antigen receptor which is expressed on a second white cell subpopulation; and (b) a second Amdex-crosslinked antibody-(phycobiliprotein or tandem dye) conjugate, prepared with an antibody which binds a second cell surface receptor expressed on the mutually exclusive second subset of white blood cells. The combination of these two types of labeled ligands produces two fluorescent-labeled cell populations in mixtures with whole blood with two distinct and non-overlapping fluorescent intensities of the same color emission. Preferably, the intensity difference between the first and second labeled ligands is greater than the intensity difference observed when two direct conjugates are used and separate intensities are observed due to the range of naturally-occurring receptor densities for the first and second cell populations in normal donors.

Cells so labeled with a phycobiliprotein or tandem dye may then be observed under a microscope, the presence of the fluorescer being diagnostic of the presence of a specific determinant site or the cells may be detected in a fluorescence-activated cell sorter (FACS).

To extend the number of fluorescence colors that can be obtained with the combination of direct and aminodextran-crosslinked antibody-fluorescent dye conjugates, and thus the numbers of white cell subpopulations that may be identified by this method, additional pairs of ligand (a) and ligand (b) may be used simultaneously employing additional phycobiliproteins, preferably where the fluorescence emission maximum of the biliproteins is separated by at least about 15 nm, and preferably by at least about 25 nm.

The use of the tandem dye molecules, such as PC5 or ECD, that can be excited with the same laser line, 488.0 nm Ar$^+$, as PE, when incorporated into the directly conjugated ligand (a) and crosslinked conjugate (b) offer yet other pairs of markers from the use of only the phycobiliproteins as marker, and thereby provide a method employing three color, two intensity per color, markers.

Alternatively, the fluorescers other than biliproteins, for example fluorescein isothiocyanate (FITC), rhodamine, dansyl and Texas Red, where the emission maxima are separated by at least about 55 nm, preferably about 58 nm., may be used in the method of this invention as a single intensity, additional color marker, directly conjugated to a ligand to provide for additional colors of fluorescence in the method of this invention.

Thus, together with a FITC (excitation, 468–505 nm, emission, 504–541 nm)—labeled ligand (e.g., monoclonal antibody) as an additional color, single intensity marker, there will be available a maximum of seven markers that can be excited simultaneously with a single laser line. This combination of seven markers can further be expanded with the use of two or more laser excitation lines, e.g., 488.0 nm Ar$^+$ and 632.8 nm He/Ne, and additional colors/intensities of fluorescent emission from direct antibody-APC (allophycocyanin, excitation, 650 nm, emission, 660 nm)/aminodextran-crosslinked antibody-APC conjugates and markers containing tandem dye conjugates of APC such as APC-Cy7 [M. Roederer et al, *Cytometry*, 24:191–197 (1996)]. Also other protein fluorophores, such as the green fluorescent proteins and blue fluorescent proteins as stated above, may also be employed in these methods [see, e.g., Handbook of Fluorescent Probes and Research Chemicals, 6th Ed., R. P. Haugland, Molecular Probes, Inc., Eugene, Oreg., 1996].

Thus, the method of the invention when employed to detect multiple subsets of white blood cells in a single-measurement quantification may be summarized as follows:

(A) providing between one to multiple pairs of WBC cell populations, the first population of each pair having a first cell surface receptor density which is substantially equivalent to, or less than, the density of a second cell surface receptor on the second population of each pair, the first receptor being found only on the first cell population of each pair, and the second receptor being found only on the second cell population of each pair, wherein the first receptor differs among each first population and the second receptor differs among each second population;

(B) providing for each first population a first ligand labeled directly with a phycobiliprotein or tandem dye, the first ligand capable of binding to the first receptor and differing among each first population; and the phycobiliprotein or tandem dye differing among each first ligand;

(C) providing for each second population a second ligand labeled with an aminodextran-(phycobiliprotein or tandem dye) conjugate, the second ligand capable of binding to the second receptor and differing among each second receptor; wherein within a pair of cell populations the phycobiliprotein or tandem dye of the conjugate is the same as the phycobiliprotein or tandem dye of the first ligand, and wherein the phycobiliprotein or tandem dye of each pair of ligands is a different color;

(D) incubating a biological sample comprising the multiple WBC cell populations with each pair of the first and the second labeled ligands for a time sufficient to permit receptor-labeled ligand complexes to form therebetween;

(E) exciting each phycobiliprotein or tandem dye in each complex with a laser excitation line to cause it to fluoresce; and (F) measuring the intensities of fluorescent emissions of each first cell population bound to each labeled first ligand and the fluorescent emissions of each second population bound to each labeled second ligand in a single measurement using flow cytometry;

wherein within each pair of cell populations, the first labeled ligand provides a fluorescent signal of the same color but quantitatively distinguishable intensity from that of the second labeled ligand, and wherein the cell populations are distinguished by detectable variations in label intensity and color.

Examples of the use of the method of this invention with single color or multiple colors of markers, e.g., phycobiliproteins or tandem dyes, are provided below. The introduction of multiple color/intensity immunofluorescence to flow cytometry has several notable advantages. It does not require as much sample; especially important when there is very little sample available, i.e., cell number is low. The cost may be less than larger panel with fewer colors/intensities. The method uses less lyse and quench reagent in preparation of whole blood samples. Less time is required for sample processing; there are fewer tubes to aliquot and handle, and isotype controls may not be needed.

In contrast to the prior art methods disclosed in U.S. Pat. No. 5,538,855, for example, the enhanced fluorescence intensity of crosslinked antibody-dye conjugates over direct antibody-dye conjugates as employed in these methods does not restrict analysis of cell subsets to cell subsets whose intrinsic receptor densities for markers of the same color result in non-overlapping fluorescent marker intensities. Rather, two different (or multiple pairs of two different) mutually-exclusive populations of white blood cells with similar intrinsic receptor densities can be analyzed simultaneously with the same color but different intensity of fluorescent markers according to this invention. To avoid overlap of fluorescence intensities of multi-intensity markers of the same color, the intensity difference must be greater than that observed due to the range of naturally-occurring receptor densities for the two targeted white blood cell subsets in normal blood donors.

The following examples illustrate various aspects of the present invention. These examples do not limit the scope of the invention, which is embodied in the appended claims.

EXAMPLE 1

Preparation of a Cross-Linked Conjugate

An exemplary cross-linked conjugate useful in the present invention was prepared as follows:

(1) a solution of Amdex in distilled water, to which buffer solution was added, was activated with sulfosuccinimidyl 4-[N-maleimidomethyl]cyclohexane-1-carboxylate (sulfo-SMCC) solution in 1×PBS. The mixture was roller mixed for about one hour at room temperature. After the mixing was completed, the reaction mixture was immediately applied to the top of a G-50 Sephadex column equilibrated with 1×PBS. The sample was eluted using 1×PBS and collected in about 2 mL fractions. Fractions of the first band, absorbing at 280 nm, contained the high molecular weight activated Amdex as was verified by Tyndall scatter with a focused visible light beam. These fractions were pooled to give sulfo-SMCC-activated Amdex;

(2) the ligand, i.e., monoclonal antibody, as activated by the addition of a solution of 2-iminothiolane in 1×PBS to antibody concentrate. The resulting solution having an antibody concentration of 15 mg/mL and an iminothiolane-to-antibody molar activation ratio of 15 was mixed at ambient temperature for about one hour. The reaction mixture was then chromatographed on a G-50 Sephadex column equilibrated with 1×PBS and the sample was eluted using 1×PBS. Peak fractions of the first band were collected and pooled;

(3) phycobiliprotein was activated by the addition of a solution of 2-iminothiolane in 1×PBS. The resulting solution having a phycobiliprotein concentration of 40 mg/mL and an iminothiolane-to-phycobiliprotein molar activation ratio of 22.5 was mixed at room temperature for about one hour. The reaction mixture was then applied to the top of a G-50 Sephadex column equilibrated with 1×PBS and the sample was eluted with 1×PBS;

(4) iminothiolane-monoclonal antibody solution was first mixed with iminothiolane-phycobiliprotein solution to which a sulfo-SMCC-5X-Amdex solution was subsequently added, or iminothiolane was first added to a sulfo-SMCC-5X-Amdex solution and the iminothiolane monoclonal antibody solution was added immediately afterwards. The entire mixture was then roller mixed overnight for about 16–24 hours. After the mixing was completed, the total volume of each mixture was determined and 0.120 times this volume of 5 mg/mL L-cysteine in 1×PBS was added to the conjugation mixture. The L-cysteine containing mixtures were then mixed for an about 15 minutes to effect blocking of any unreacted sulfo-SMCC moieties. Lastly, iodoacetamide in 1×PBS in the amount of 0.120 times the total mixture volume and 1M borate buffer solution, pH 9.8, in the amount of 0.020 times the total mixture volume were added to the conjugation mixture. The resulting mixture was mixed for about 30 minutes to block any unreacted sulfhydryl groups;

After blocking, the mixture was purified into its components by size exclusion chromatography as follows: the total volume of the conjugation mixture was reduced to about 1.0 to 1.5 mL. The sample was then applied to the top of a Bio-Gel A-5 m or A-15 m agarose column (2.5 cm×48 cm) equilibrated with 1×PBS and chromatographed using 1×PBS as eluant. Eluant fractions of about 2–4 mL volume were collected. The fractions were monitored at 280 nm. The fractions of the first band collected for the antibody-Amdex-PE conjugate were analyzed spectrophotometrically at 565 and 280 nm using a 1 cm path length cell. The concentration of PE in mg/mL in the conjugate was derived from the absorbance at 565 nm. The active antibody concentration in the conjugate was determined by an ELISA assay and $A_{280}$ values corrected for absorbance by PE.

EXAMPLE 2
Preparation of Anti-CD8αβ Antibody-PC5 Conjuaate

Direct monoclonal antibody-fluorochrome (PE, PC5, ECD) conjugates are commercially available for most antibodies from Coulter Corporation or Immunotech, as prepared by established procedures of conjugation reactions of iminothiolane activated PE (or PC5; ECD) with sulfo-SMCC activated antibody or iminothiolane activated PE (or PC5; ECD) with DTT (dithiothreitol) reduced antibody. The molar ratio of monoclonal antibody:fluorochrome in these conjugates is about 1:1. Conjugation of IgG monoclonal antibody to PC5 was accomplished by sulfosuccinimidyl 4-[N-maleimidomethyl]cyclohexane-1-carboxylate (sulfo-SMCC) activation of PC5 and activation of antibody by reduction of disulfide bonds in the hinge region with dithiothreitol (DTT).

A. Activation of Monoclonal Antibody (MCA)

For 50 mg of MCA at a concentration of 14.04 mg/mL, 3.549 mL of MCA concentrate were required. A 15.4 mg/mL solution of DTT in 1×PBS was prepared and used at an activation ratio of DTT: MCA=300:1. Thus, to make a total volume of 10 mL with 5 mg/mL of MCA, 5.451 mL of 1×BBS buffer (20 mM borate, 150 mM sodium chloride, pH 8.8) were placed in a reaction vial, to which were added 3.549 mL of MCA solution with stirring at 25° C. and then slowly added 1.000 mL of DTT solution. The reaction mixture in a vial was incubated at 25° C. for 20 minutes, after which 2.5 mL of MES (2-[N-morpholino] ethanesulfonic acid) quenching buffer (50 mM MES, 5.0M sodium perchlorate, 4 mM EDTA (ethylenediaminetetraacetic acid), pH 5, were added and the reaction mixture was incubated 2 minutes further. Then, immediately the activated MCA sample was applied to the top of a 200 mL G-50 Sephadex column, equilibrated with MES column buffer (50 mM MES, 100 mM sodium perchlorate, 4 mM EDTA, pH 6.0). The activated MCA was eluted from the column with MES buffer and fractions of the first peak absorbing at 280 nm were collected. The activated MCA concentration in mg/mL was determined by the $A_{280}$ value. 34 mL of activated MCA solution at 1.394 mg/mL (47.4 mg) were obtained.

B. Activation of PC5 with sulfo-SMCC

PC5, the PE (R-phycoerythrin (red algae))-5'-cyanine tandem conjugate, prepared as described in U.S. Pat. No. 4,542,104 and U.S. Pat. No. 5,272,257 incorporated by reference herein. For 55 mg of PC5 at a concentration of 14.69 mg/mL in 1×BBS buffer, 3.744 mL of the PC5 concentrate were required. A 4.5 mg/mL solution of sulfo-SMCC in 1×BBS buffer was prepared and used at an activation ratio of sulfo-SMCC: PC5=40:1. Thus, to make 5 mg/mL of PC5 at a total volume of 11 mL, 5.936 mL of 1×BBS buffer were placed in a reaction vial, to which were added 3.744 mL of PC5 solution with stirring at 25° C. and then, slowly added 0.44 mL of NEM (N-ethyl maleimide, 31.25 mg/mL in 1×BBS buffer) solution. The reaction mixture in the vial was incubated for 30 minutes. Then, 0.88 mL of sulfo-SMCC solution (4.5 mg/mL) was added to the mixture which was incubated for a further 60 minutes. At the end of the last incubation period, 1.1 mL of 1M ammonium chloride in 1×BBS buffer were added to the mixture, and further incubated for 2 minutes. Then immediately the activated PC5 was loaded onto a 200 mL G-50 Sephadex column, equilibrated with MOPS (3-[N-morpholino] propanesulfonic acid) column buffer (50 mM MOPS, 100 mM sodium perchlorate, 4 mM EDTA, pH 7.0). The activated PC5 was eluted from the column with MOPS buffer and the first colored peak off the column was collected. The concentration of 1.962 mg/mL of activated PC5 was determined as $A_{565.5}/8.167$. The activated PC5 was diluted to 1.5 mg/mL with MOPS buffer to give 32.7 mL total volume.

C. Conjugation of MCA with PC5

For conjugation, equal volumes (32.7 mL) of activated MCA at 1.4 mg/mL and activated PC5 at 1.5 mg/mL were mixed by adding activated MCA into stirring activated PC5. The reaction mixture was incubated at 25° C. for 2 hours. At the end of the mixing period, 2.642 mL of 31.25 mg/mL NEM in 1×BBS buffer were further added to the reaction mixture, which was roller mixed for an additional 5 minutes.

D. Purification of MCA-PC5 conjugate

A Superdex 200 prep grade column (3.4 mL of column per mg of MCA or 318 mL) equilibrated with 1×PBS, 2 mM EDTA, pH 7.2 buffer was prepared. The MCA-PC5 reaction mixture was concentrated to less than 2% of the Superdex pg column volume, 4.33 mL. The sample was loaded onto the Superdex 200 pg column, and eluted with 1×PBS, 2 mM EDTA, pH 7.2 buffer at 119 mL/hr. The $A_{280}/A_{565.5}$ ratio was calculated for each fraction. All fractions with ratios from 0.43 until two fractions before the free PC5 eluates were pooled. For example, the pooled CD8αβ-PC5 fractions, 25 mL, were concentrated to a volume of 3.45 mL, less than 1% of the column volume, by using an Amicon YM30 membrane, diafiltering the concentrate with 1×PBS, 0.1% sodium azide, 0.1 mM EDTA buffer, and centrifuging the CD8αβ-PC5 conjugate at 1800×g for 15 minutes at 4° C. A 100-fold dilution of this pooled sample gave $A_{565.5}$= 0.4809 or (/8.167)×100=5.888 mg/mL PC5 and 20.31 mg total PC5 in the CD8αβ-PC5 conjugate, and $A_{280}$=0.1513 or [0.4809/5.476 (PC5's $A_{565.5}/A_{280}$)]×100=6.349 mg/mL CD8αβ and 21.90 mg total CD8αβ in the CD8αβ-PC5 conjugate. The molar ratio of PC5/CD8αβ is therefore (20.31 mg PC5/240,000)//(21.90 mg CD8αβ/160,000)= 0.618. A corrected F/P ratio based on the formula, MCA:PC5=[$A_{280}/A_{565.5}$ (conjugate)−$A_{280}/A_{565.5}$ (dye)]× 8.77, is 0.864. Similar methods were used to prepare a CD4-ECD conjugate having an F/P ratio of 0.96. Alternatively, the direct MCA-dye conjugate could be prepared by sulfo-SMCC activation of antibody, 2-iminothiolane activation of dye (e.g., PE or PC5), followed by conjugation and purification, as described in Example 1 above (see also, Example II of U.S. patent application Ser. No. 08/847,941, cited above and incorporated by reference herein).

Figure 1B:
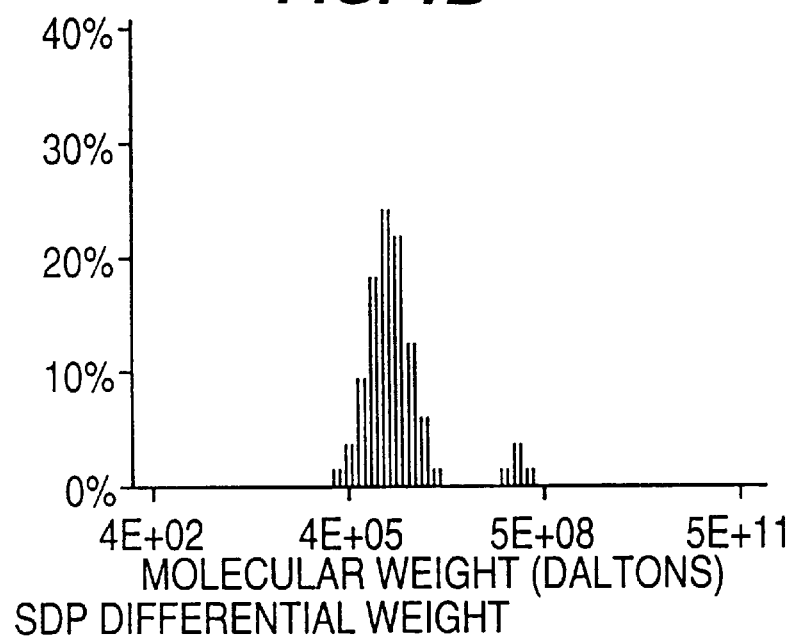
FIG. 1B is a histogram showing relative weight percent (mass %) of Amdex molecules vs their molecular weight or SDP differential weight distribution of a 5X-Amdex sample suitable for use in preparation of antibody-5X-Amdex-PE, PC5, or ECD conjugates which yield enhanced fluorescence emission intensities, after sulfo-SMCC activation and purification as measured on the Coulter analyzer, as described for FIG. 1A.

EXAMPLE 3
Properties of Preferred Aminodextran in Preparation of Antibody-Aminodextran-Phycobiliprotein Conjugates The procedure for preparation of conjugates was similar to that described in U.S. Pat. No. 5,527,713 issued Jun. 18, 1996 to prepare conjugates of anti-CD3 antibody with aminodextran, either 1X-Amdex or 5X-Amdex. However, in this example, two different proteins, one, a monoclonal antibody and the other, a fluorescent protein, were conjugated simultaneously to the aminodextran as described for the fluorescent dye, PE, in Example 1. The requirements for the aminodextran used in the preparation of the conjugates can be defined more precisely herein. Syntheses of 5X-Amdex have been described in U.S. Pat. Nos. 5,466,609; 5,527,713; 5,552,086; 5,639,620; and 5,658,741, all incorporated by reference herein. The preferred 5X-Amdex has an average molecular weight (MW) as high as possible and as nearly equal to the dextran (preferably *Leuconostoc mesenteroides* strain B-512) of 2M average MW, which was used as a starting material in all experiments. Average MW lower than 2M were obtained for the product 5X-Amdex in all preparations due to the competing reaction of aminolysis of the dextran during amination of oxidized dextran, dextran aldehyde, with 1,3-diaminopropane. No reduction in average MW was observed after the periodate oxidation of dextran, as measured for appropriately diluted samples on the Coulter N4MD Sub-Micron Particle Analyzer. Best results for antibody-5X-Amdex-dye conjugates were obtained when the average MW of 5X-Amdex was equal to or greater than 350,000 Daltons. Material which analyzed as about ⅐ to ⅑ degree of substitution of dextran by two diaminopropane molecules per oxidized glucose residue, but showed an average MW less than about 350,000 Daltons did not produce conjugates capable of fluorescence amplification. With the preferred 5X-Amdex, activation of the aminodextran with sulfo-SMCC, separation by chromatography on a G-50 Sephadex column, and selection of material under the first narrow peak detected by an $A_{280}$ monitor served to yield sulfo-SMCC-activated 5X-Amdex with an even higher average MW in the range 1 to 2M Daltons. The relative weight (mass)-average MW distribution of a 5X-aminodextran sample suitable for use in preparation of antibody-5X-Amdex-PE, PC5, or ECD conjugates which yield enhanced fluorescence emission intensities, before and after sulfo-SMCC activation and purification as measured on a Coulter N4MD Sub-Micron Particle Analyzer, is shown in FIGS. 1A and 1B.

EXAMPLE 4
Trial 1 conjugation with total protein, CD8αβ and PC5, to 5X-Amdex weight ratios of 3:1 and an antibody:5X-Amdex weight ratio of 1:2.3

A. Activation of aminodextran with sulfo-SMCC 0.437 mL of a 22.867 mg/mL solution of 5X-Amdex in DW, to which 0.023 mL of 20×PBS buffer solution were added to make a 1×PBS solution, were activated with 0.180 mL of 10 mg/mL sulfo-SMCC solution in 1×PBS. The mixture was roller mixed for about one hour at room temperature. After the mixing was completed, the reaction mixture was immediately applied to the top of a 60 mL G-50 Sephadex column equilibrated with 1×PBS. The sample was eluted using 1×PBS and collected in about 2 mL fractions. Fractions of the first band absorbing at 280 nm contained the high molecular weight activated 5X-Amdex as was verified by Tyndall scatter with a focused visible light beam (Model 650, Cambridge Instruments, Inc., Buffalo, N.Y.). These fractions were pooled to give about 3.7 mL total sulfo-SMCC-activated 5X-Amdex.

B. Activation of Antibody

CD8αβ monoclonal antibody was activated by the addition of 0.065 mL of a 2 mg/mL solution of iminothiolane in 1×PBS and 0.440 mL 1×PBS to 0.162 mL of CD8β concentrate (61.67 mg/mL). The resulting solution which had an antibody concentration of 15 mg/mL and an iminothiolane molar concentration fifteen-fold larger was mixed at ambient temperature for about one hour. The reaction mixture was then chromatographed on a 60 mL G-50 Sephadex column equilibrated with 1×PBS and the sample was eluted using 1×PBS. The peak fraction of the first band yielded about 3.3 mL of 3.407 mg/mL antibody solution which contained a total of 11.24 mg IT-CD8αβ antibody derivative.

C. Activation of PC5

PC5 concentrate, prepared as described in U.S. Pat. No. 4,542,104 and U.S. Pat. No. 5,272,257 incorporated by reference herein, was activated by the addition of 0.232 mL of a 2 mg/mL solution of iminothiolane in 1×PBS and 0.126 mL 1×PBS to 0.542 mL of PC5 concentrate (66.48 mg/mL). The resulting solution which had a PC5 concentration of 40 mg/mL and an iminothiolane molar concentration 22.5-fold larger was mixed at room temperature for about one hour. The reaction mixture was then applied to the top of a 60 mL G-50 Sephadex column equilibrated with 1×PBS and the sample was eluted with 1×PBS. The first band peak fraction gave about 4.3 mL of 6.683 mg/mL PC5 at an $A_{565}/A_{280}$ ratio of 6.0821, which contained a total of 28.738 mg IT-PC5.

D. Conjugation of IT-CD8αβ and IT-PC5 to sulfo-SMCC-5X-Amdex

3:1 total protein:5X-Amdex weight ratios: 1.257 mL of 3.407 mg/mL IT-CD8αβ solution (about 4.287 mg antibody) were first mixed with 3.849 mL of 6.683 mg/mL IT-PC5 solution (about 25.713 mg PC5), to which were added 3.7 mL of sulfo-SMCC-5X-Amdex solution (about 10 mg 5X-Amdex) and the entire mixture was roller mixed overnight for 16–24 hours. After the mixing was completed, the total volume of the mixture was determined and 0.120 times this volume of 5 mg/mL L-cysteine in 1×PBS was added to each conjugation mixture. The L-cysteine containing mixture was then mixed for an additional 15 minutes to effect blocking of any unreacted sulfo-SMCC moieties. Lastly, 20 mg/mL iodoacetamide in 1×PBS in the amount of 0.120 times the total mixture volume and 1M borate buffer solution, pH 9.8, in the amount of 0.020 times the total mixture volume were added to the mixture. The resulting mixture was mixed for about 30 minutes to block any unreacted sulfhydryl groups.

E. Purification of CD αβ-5X-Amdex-PC5 conjugates

Figure 2:
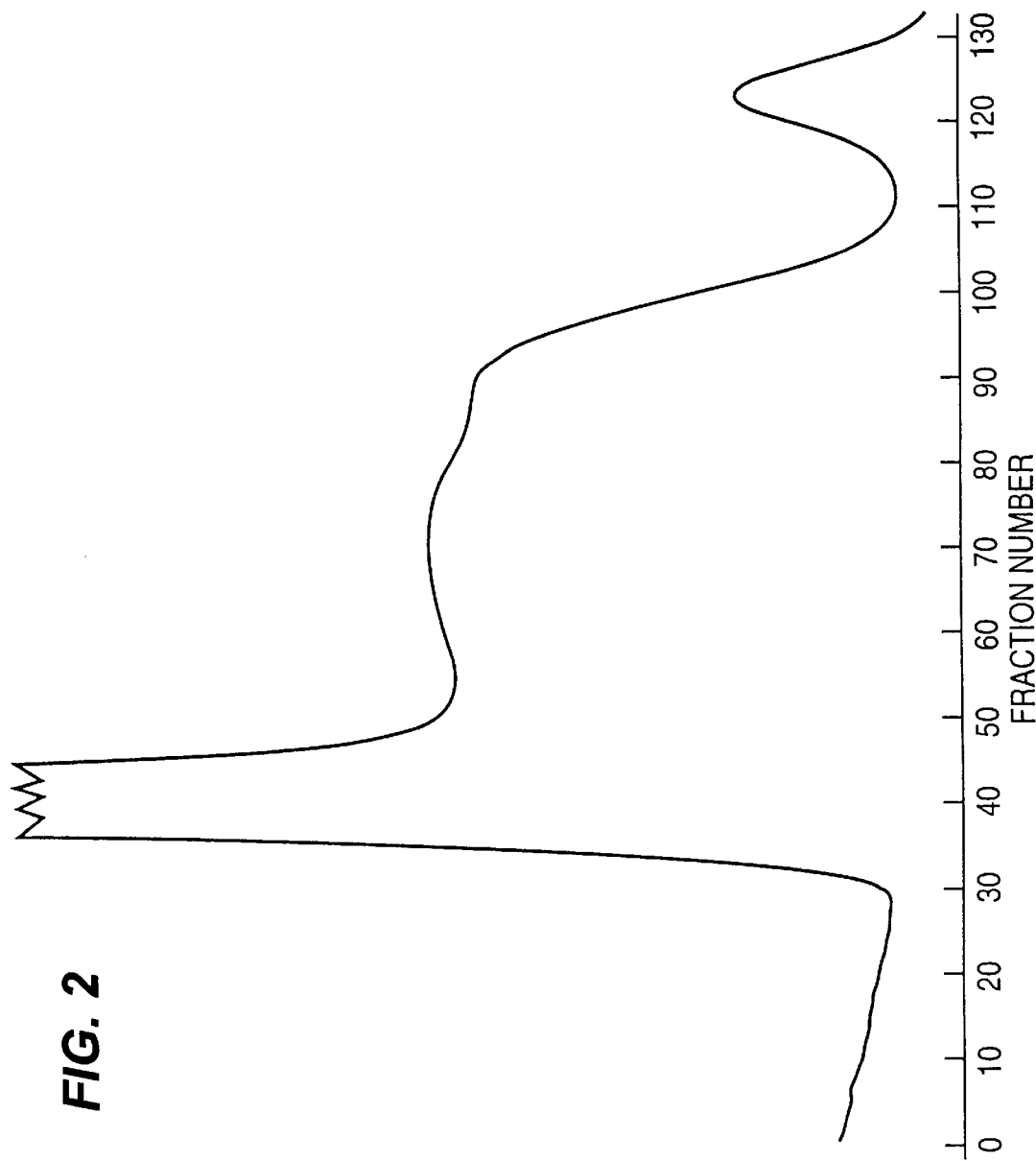
FIG. 2 is a chromatogram showing the $A_{280}$ vs fraction number monitored using a LKB 2138 Uvicord S monitor operating at 280 nm for purification of CD8αβ-5X-Amdex-PC5 conjugation mixtures.

The total volume of conjugation mixture was reduced to about 1.5 mL by centrifuging an Amicon Centri-Prep 30 tube containing the sample for about 30 minutes at 2200 rpm using a refrigerated Beckman J-6B centrifuge. The sample was placed on the top of a Bio-Gel A-15 m agarose column (2.5 cm×48 cm) equilibrated with 1×PBS and chromatographed using 1×PBS as eluant. Eluant fractions of about 1.8 mL volume were collected using a Pharmacia LKB FRAC-100 collector operating in the drop collection mode. The fractions were monitored using a LKB 2138 Uvicord S monitor operating at 280 nm. A chromatogram showing the $A_{280}$ versus fraction number recording is displayed in FIG. 2. The first narrow, intense band eluted from the column contained the CD8αβ-aminodextran-PC5 conjugate. A second lower intensity broad band and third band, both of less than one-third the intensity of the first peak, contained ~1:1 PC5: aminodextran conjugate and excess PC5. A medium-to-low intensity, well-separated fourth band was attributed to low molecular weight excess blocking reagents.

The fractions collected for the CD8αβ-5X-Amdex-PC5 conjugate were analyzed spectrophotometrically at 565.5 and 280 nm using, a 1 mm path length cell. The concentration of PC5 in mg/mL in the conjugate was derived from the absorbance at 565.5 nm by using the formula, $A_{565.5}/8.167$. Antibody concentrations were determined from the corrected $A_{280}$ value. The active CD8αβ antibody concentration in the conjugate was determined by an ELISA assay for IgG1 antibody; however, assay results appear to show interference from non-antibody parts of the conjugate. Thus, $A_{280}$ values corrected for the PC5 contribution were used to obtain antibody concentrations. Data for fractions 36 to 46 under the first narrow peak in trial 1 are listed in Table I.

TABLE I

| Fraction | $A_{565.5}$ | $A_{280}$ | $A_{565.5}/A_{280}$ | PC5, mg/mL | CD8αβ, mg/mL | CD8αβ, µg/mL, ELISA |
|---|---|---|---|---|---|---|
| 36 | 0.0891 | 0.0344 | 2.59 | 0.109 | 0.193 | <0.016 |
| 37 | 0.2661 | 0.0959 | 2.77 | 0.326 | 0.507 | <0.016 |
| 38 | 0.7280 | 0.2450 | 2.97 | 0.891 | 1.212 | 0.029 |
| 39 | 1.1681 | 0.3744 | 3.12 | 1.430 | 1.758 | 0.042 |
| 40 | 1.1810 | 0.3646 | 3.24 | 1.446 | 1.639 | 0.043 |
| 41 | 0.8906 | 0.2648 | 3.36 | 1.090 | 1.134 | 0.040 |
| 42 | 0.5169 | 0.1452 | 3.56 | 0.633 | 0.573 | 0.025 |
| 43 | 0.2720 | 0.0715 | 3.81 | 0.333 | 0.252 | 0.019 |
| 44 | 0.1637 | 0.0397 | 4.13 | 0.200 | 0.118 | <0.016 |
| 45 | 0.1160 | 0.0260 | 4.46 | 0.142 | 0.063 | <0.016 |
| 46 | 0.0915 | 0.0191 | 4.79 | 0.112 | 0.035 | <0.016 |

TABLE I-continued

F. Anialyses for IgG1 and IgM Antibodies by ELISA

Following a previous method, ENZYME-IMMUNOASSAY, E. T. Maggio, CRC Press, Boca Raton, Fla., 1985, pp 181–196, microtiter plates (Corning modified flat bottom ELISA plates) were coated with 100 µL of affinity-purified goat anti-mouse IgG1 or IgM (Southern Biotechnology Associates, Inc.), diluted to 0.6 µg/mL in 0.2M carbonate buffer, pH 9.6, overnight at 4° C. After washing with 1×PBS, pH 7.2, containing 0.05% Tween 20, the plates were saturated with PBS containing 1% BSA and incubated for 90min at room temperature. Dilutions of antibody-5X-Amdex-PE conjugate samples were made in 1% BSA/PBS and 100 µL of each were added to the plate, which was then incubated for one hour at room temperature. Dilutions of the IgG1 and IgM antibody standards between 7.8 and 250 ng/mL, and 15.6 and 500 ng/mL, respectively, were used for calibration curves. After washing the plates, 100 µL of horseradish peroxidase (HRP)-conjugated goat anti-mouse Ig (Cappel), diluted in PBS were added and incubated for one hour at room temperature. The plates were washed and reactions were revealed by the addition of 200 µL of ABTS, 2,2'-azino-bis (3-ethylbenzthiazoline-6-sulfonic acid (Sigma), at 0.2 mg/mL in 0.2M sodium citrate buffer, pH 4.0, and 0.02% hydrogen peroxide. After a one hour incubation at room temperature, the plates were read on a V MAX microplate reader (Molecular Devices) at 405 nm using 490 nm as a reference wavelength. Semi-log plots of absorbance versus concentration were used to prepare IgG1 and IgM antibody standard linear regression curves. The antibody concentration in the samples was calculated by using absorbance values in the linear range of the standard curve.

G. Estimation of Molecular Weights of Antiibody-Aminodextran-PE Conjugates

Blue dextran (Sigma, T-2M) was applied to a Bio-Gel A-15 m column that was used to purify the antibody-aminodextran-PE conjugates, eluted from the column with 1×PBS, monitored by $A_{280}$, and collected at the same drop count of 60 drops/fraction. The first narrow peak (about fraction 40) in the elution profile of antibody-aminodextran-dye conjugates occurred in the same fraction as the first narrow peak in the elution profile of blue dextran. Therefore, we estimate the conjugates to have a molecular weight of 2,000,000 Daltons or more. The void volume with an A-15 m agarose column is estimated to contain dextran or dextran derivatives of molecular weight, 15 million/4=3.75 million, or higher. Chromatograms obtained for the antibody-aminodextran-PE, PC5, or ECD conjugates applied to an A-15 m agarose column instead of an A-5 m agarose column that was used in previous work, gave a much better separation of the shoulder to the first main band from the first band, allowing better purification of the conjugates.

EXAMPLE 5

Preparation of Anti-CD4 Antibody-5X-Aminodextran-ECD Conjugates

The procedures were the same as those outlined for the preparation of the CD8αβ-5X-Amdex-PC5 conjugate in Example 4, except anti-CD4 antibody, also of the IgG1 class, was activated with IT and used in the conjugation instead of CD8αβ antibody, and the tandem PE-Texas red or ECD fluorescent dye was used instead of PC5. In trial 2, IT-ECD (7.657 mg), IT-CD4 (1.272 mg) were mixed with sulfo-SMCC-5X-Amdex (5 mg) at concentrations of 1.11, 0.184, and 0.725 mg/mL, respectively, during conjugation. The IT-ECD ($A_{565.5}/A_{280}$) ratio was 5.296. The conjugation mixture was concentrated to about 1.5 mL and applied to the top of an A-15 m column. Data for fractions collected at about 3.6 mL per fraction under the first narrow peak in trial 2 are listed in Table III.

TABLE III

| Fraction | $A_{565.5}$ | $A_{280}$ | $A_{565.5}/A_{280}$ | ECD, mg/mL | CD4, μg/mL, ELISA |
|---|---|---|---|---|---|
| 18 | 0.0218 | 0.0071 | 3.06 | 0.027 | |
| 19 | 0.0714 | 0.0201 | 3.56 | 0.087 | |
| 20 | 0.0472 | 0.0122 | 3.87 | 0.058 | |
| pool | | | | 0.567 | 1.46 |

EXAMPLE 6

Preparation of Anti-CD56 (or CD4) Antibody-5X-Aminodextran-PE Conjugates

Again, the procedures were the same as those outlined for the CD8αβ-5X-Amdex-PC5 conjugate in Example 4, except anti-CD56 (NKH-1) or -CD4 antibody of the IgG class and PE were activated with IT and used in the conjugation instead of CD8αβ antibody and PC5. In trial 3, the reactants, 2.822 mL of 8.50 mg/mL IT-PE (23.987 mg) were first mixed with 5.4 mL of sulfo-SMCC-5X-Amdex (3.333 mg) solution, to which were then added 2.10 mL of 1.922 mg/mL IT-CD56 (4.036 mg). The IT-PE ($A_{565}/A_{280}$) ratio was 5.800. The conjugation mixture was concentrated to about 1.5 mL and applied to the top of an A-15 m column. Data for fractions collected at 1.8 mL per fraction under the first narrow peak in trial 3 are listed in Table IV.

TABLE IV

| Fraction | $A_{565.5}$ | $A_{280}$ | $A_{565.5}/A_{280}$ | PE, mg/mL | CD56, mg/mL | CD56, μg/mL, ELISA |
|---|---|---|---|---|---|---|
| 36 | 0.1302 | 0.0421 | 3.10 | 0.159 | 0.190 | 1.37 |
| 37 | 0.3752 | 0.1115 | 3.37 | 0.459 | 0.450 | 4.38 |
| 38 | 0.6978 | 0.1964 | 3.55 | 0.854 | 0.729 | 11.4 |
| 39 | 0.7182 | 0.1928 | 3.72 | 0.879 | 0.657 | 12.4 |
| 40 | 0.4911 | 0.1256 | 3.90 | 0.601 | 0.387 | 8.33 |
| 41 | 0.3003 | 0.0732 | 4.10 | 0.368 | 0.200 | 4.58 |
| 42 | 0.1998 | 0.0462 | 4.33 | 0.245 | 0.108 | 3.59 |
| 43 | 0.1508 | 0.0336 | 4.49 | 0.185 | 0.069 | 2.77 |
| 44 | 0.1251 | 0.0271 | 4.62 | 0.153 | 0.049 | 2.35 |
| 45 | 0.1117 | 0.0236 | 4.72 | 0.137 | 0.039 | 4.16 |

In trial 4, 3.117 mL of 8.25 mg/mL IT-PE (25.715 mg) were first mixed with 3.3 mL of sulfo-SMCC-5X-Amdex (10 mg) solution, to which were then added 1.434 mL of 2.991 mg/mL IT-CD4 (4.287 mg). The conjugation mixture was concentrated to about 1.5 mL and applied to the top of an A-15 m column. Data for fractions collected at 1.8 mL per fraction under the first narrow peak in trial 4 are listed in Table V.

TABLE V

| Fraction | $A_{565.5}$ | $A2_{280}$ | $A_{565.5/A280}$ | PE, mg/mL | CD4, mg/mL | CD4, μg/mL, ELISA |
|---|---|---|---|---|---|---|
| 36 | 0.0797 | 0.0234 | 3.41 | 0.098 | 0.093 | 1.11 |
| 37 | 0.2044 | 0.0596 | 3.43 | 0.250 | 0.234 | 2.85 |
| 38 | 0.3205 | 0.0900 | 3.56 | 0.392 | 0.332 | 5.85 |
| 39 | 0.3387 | 0.0920 | 3.68 | 0.415 | 0.321 | 8.74 |
| 40 | 0.2714 | 0.0702 | 3.86 | 0.332 | 0.222 | 4.83 |
| 41 | 0.1948 | 0.0475 | 4.10 | 0.239 | 0.130 | 3.67 |
| 42 | 0.1436 | 0.0337 | 4.26 | 0.176 | 0.083 | 2.48 |
| 43 | 0.1115 | 0.0254 | 4.39 | 0.137 | 0.057 | 2.01 |

The following Examples 7–10 below demonstrate a comparison of direct and aminodextran-crosslinked fluorophore-antibody conjugates as cell markers in flow cytometry.

EXAMPLE 7

Flow Cytometric Analyses of Whole Blood with CD8αβ-PC5 and CD8αβ-5X-Amdex-PC5 Conjugates CD8αβ-PC5 at an antibody concentration of 5.71 mg/mL and fractions of CD8αβ-5X-Amdex-PC5 conjugates from trial 1 were titered, starting at 3 μg of antibody in the conjugate per tube. Amounts of antibody for the titers were determined from corrected $A_{280}$ values for the conjugates. Dilutions were added to 100 μL of whole blood and incubated for 60 min at room temperature. The mixtures with blood were lysed and quenched on the Coulter Q-PREP, washed once with 1×PBS (by addition of 1 mL of 1×PBS, centrifugation at 500 g for 5 min, discarding supernatant, and resuspension of cells in 1 mL of 1×PBS) and run on a flow cytometer (Coulter Epics XL-MCL).

Figure 3B:
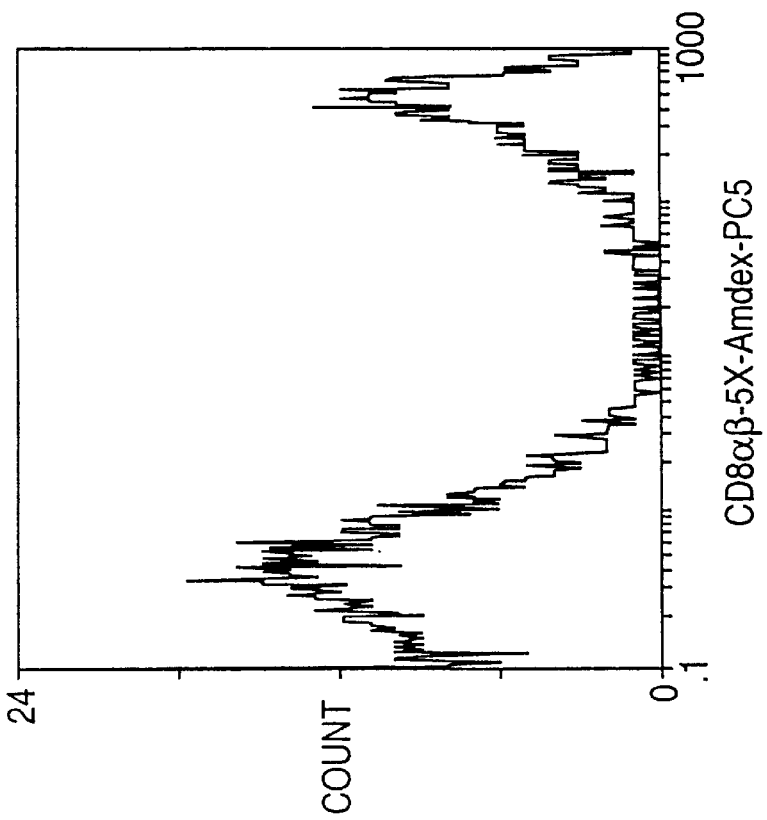
FIG. 3B is a histogram plotting cell count vs. MFI and showing the ability of the CD8αβ-5X-Amdex-PC5 conjugate as a fluorescent marker containing more than two PC5 molecules per dextran molecule to enhance the mean channel PC5 fluorescence intensity of the direct CD8αβ- PC5 conjugate. Staining of scatter gated CD8αβ+ lymphocytes is shown from analysis of 100 μL of whole blood from a normal donor, which was stained with 10 μL containing 2.5 μg of CD8αβ-5X-Amdex-PC5 as ligand. The histograms show that the crosslinked conjugate has 3.5-fold higher fluorescence intensity on CD8αβ+ lymphocytes.
Figure 3A:
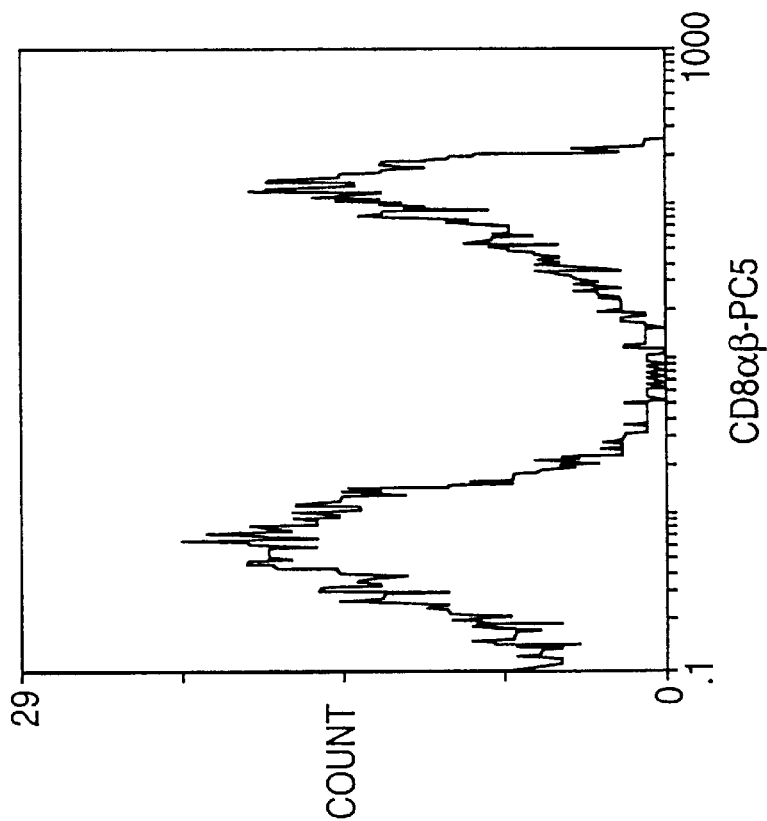
FIG. 3A is a histogram plotting cell count (number of cells) vs. mean channel fluorescence intensity (MFI) and showing the MFI of the direct CD8αβ-PC5 conjugate which contains 0.86 PC5 per antibody molecule. Staining of scatter gated CD8αβ+ lymphocytes is shown from analysis of 100 μL of whole blood from a normal donor, which was stained with 10 μL containing 2.5 μg of CD8αβ-PC5 as ligand.

The ability of CD8αβ-5X-Amdex-PC5 conjugate as a fluorescent marker containing more than two PC5 molecules per dextran molecule to enhance the mean channel PC5 fluorescence intensity obtained with the direct CD8αβ-PC5 conjugate which contains 0.86 PC5 per antibody molecule, is shown in the histograms of FIGS. 3A–3B, RHS versus LHS. The two histograms of FIGS. 3A and 3B show staining of scatter gated lymphocytes. 100 μL of whole blood from a normal donor was stained with 10 μL containing 2.5 μg of CD8αβ antibody as LHS, CD8αβ-PC5 or RHS, CD8αβ-5X-Amdex-PC5. The histograms show that the crosslinked conjugate has 3.5-fold higher fluorescence intensity on CD8αβ+ lymphocytes.

In another run, it was found that the mean channel fluorescence intensity of labeled T cells could be enhanced up to 8-fold by examining various fractions of trial 1, CD8αβ-5X-Amdex-PC5 conjugate as the fluorescent marker. Titers of the control, CD8αβ-PC5, and the sample, CD8αβ-5X-Amdex-PC5, with the same instrument settings were run and the results, mean channel PC5 fluorescence intensities and MFI ratios, sample fraction-to-control at same titers, are presented in Table VI for another normal donor.

TABLE VI

| CD8αβ, μg | Control | 36 | 37 | 38 | 39 | 40 | 41 | 42 | 43 |
|---|---|---|---|---|---|---|---|---|---|
| | Mean Channel PC5 Fluorescence Intensities Fraction | | | | | | | | |
| 3 | 53 | 265 | 325 | 379 | 419 | 376 | 377 | 381 | |
| 2.5 | 53 | 282 | 303 | 352 | 334 | 335 | 357 | 368 | |
| 2 | 55 | 236 | 266 | 302 | 293 | 311 | 319 | 320 | |
| 1.5 | 51 | 194 | 226 | 252 | 240 | 213 | 265 | 292 | 336 |

TABLE VI-continued

| CD8αβ, μg | Control | 36 | 37 | 38 | 39 | 40 | 41 | 42 | 43 |
|---|---|---|---|---|---|---|---|---|---|
| 1 | 50 | 174 | 196 | 178 | 183 | 166 | 197 | 216 | 262 |
| 0.5 | 51 | 93 | 130 | 134 | 132 | 155 | 112 | 117 | 177 |
| MFI Ratios, Fraction/Control | | | | | | | | | |
| 3 | 1.0 | 5.0 | 6.1 | 7.1 | 7.9 | 7.1 | 7.1 | 7.1 | |
| 2.5 | 1.0 | 5.3 | 5.7 | 6.6 | 6.3 | 6.3 | 6.7 | 6.9 | |
| 2 | 1.0 | 4.3 | 4.8 | 5.5 | 5.3 | 5.7 | 5.8 | 5.8 | |
| 1.5 | 1.0 | 3.8 | 4.4 | 4.9 | 4.7 | 4.2 | 5.2 | 5.7 | 6.6 |
| 1 | 1.0 | 3.5 | 3.9 | 3.6 | 3.7 | 3.3 | 4.0 | 4.3 | 5.3 |
| 0.5 | 1.0 | 1.8 | 2.5 | 2.6 | 2.6 | 3.0 | 2.2 | 2.3 | 3.5 |

MFI ratios corrected for the F/P ratio, 0.860, of the control, direct CD8αβ-PC5 conjugate, were about 16–17% higher than values listed in Table VI. Signal-to-noise and MFI ratios for control versus sample are summarized in the graphs of FIGS. 4A–4B for trial 1, fraction 42.

Figure 6B:
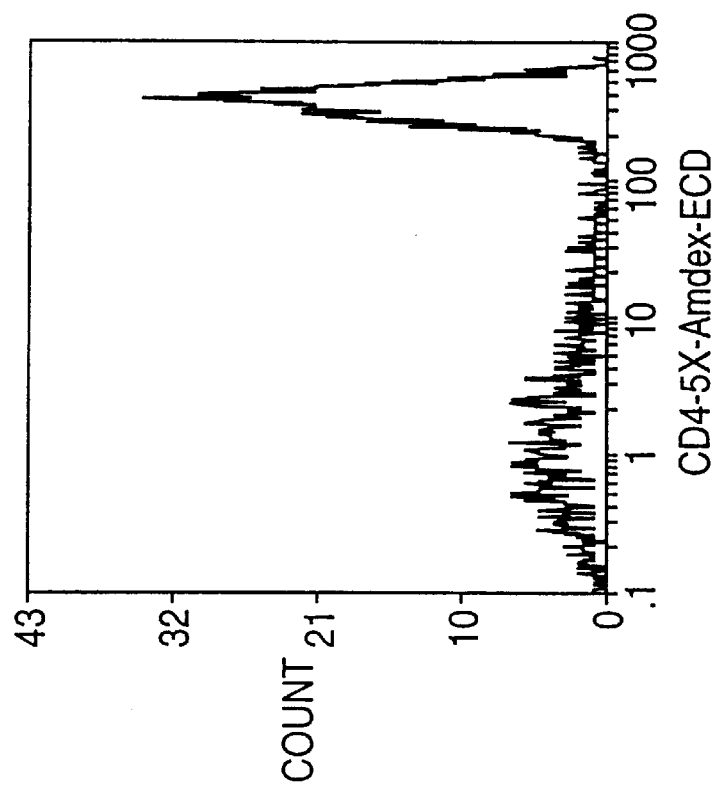
FIG. 6B is a histogram for the 0.03 μg CD4 antibody titer of the CD4-5X-Amdex-ECD ligand.
Figure 6A:
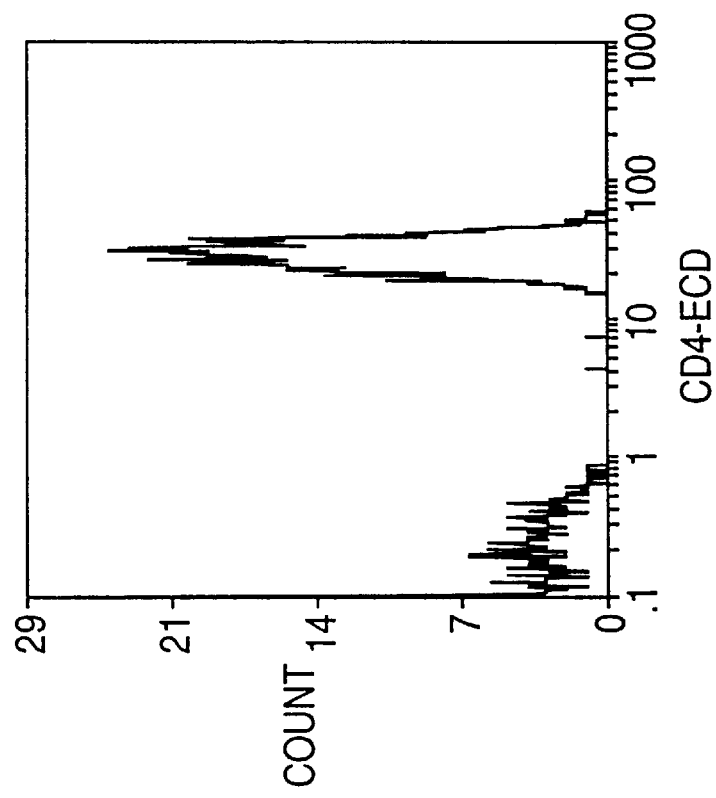
FIG. 6A is a histogram for the 0.03 μg CD4 antibody titer of the CD4-ECD ligand.

EXAMPLE 8
Flow CYtometric Analyses of Whole Blood with CD4-ECD and CD4-5X-Amdex-ECD Conjugates CD4-ECD and a single pooled sample of CD4-5X-Amdex-ECD conjugates from trial 2 were titered starting at 0.5 μg (based on ELISA analysis for CD4-5X-Amdex-ECD and $A_{280}$ value for CD4-ECD) per tube in the same way as in the previous example. The results are shown in FIG. 5 for the signal-to-noise ratio and mean channel ECD fluorescence intensities for the CD4+ lymphocytes with the direct and crosslinked antibody-ECD conjugates. The MFI ratios, maximizing at 9.7 were calculated from the mean channel positions. Using the F/P ratio of 0.96 for the CD4-ECD conjugate, the corresponding maximum MFI ratio is 10.1. Representative histograms for the 0.03 μg CD4 antibody titer of each conjugate, CD4-ECD on LHS and CD4-5X-Amdex-ECD on RHS, are displayed in FIGS. 6A–6B.

EXAMPLE 9
Flow Cytometric Analyses of Whole Blood with CD56-PE and CD56-5X-Amdex-PE Conjugates CD56 (NKH-1) antibody conjugates were prepared for use in demonstrating multi-marker, enhanced and non-enhanced PE, flow cytometric analysis. Thus, establishment of fluorescence amplification for the CD56-5X-Amdex-PE conjugate was first needed. Titers of the control, CD56-PE at an antibody concentration of 0.125 mg/mL, and the samples, CD56-5X-Amdex-PE from trial 3, starting with 8 μg of antibody per tube, were mixed for 30 min at room temperature with 100 μL whole blood from one blood donor. Concentrations of CD56 antibody in the conjugates were based on $A_{280}$ values. The samples were subjected to Q-PREP lyse and quench, followed by washing with 1×PBS. Mean channel PE fluorescence intensities relative to the control, obtained on the Coulter EPICS XL-MCL flow cytometer with the same instrument settings, are listed in Table VII and show a maximum enhancement of 14-fold over the control.

TABLE VII

| CD56, μg | Control | 37 | 39 | 40 | 41 | 42 |
|---|---|---|---|---|---|---|
| Mean Channel PE Fluorescence Intensities Fractions | | | | | | |
| 8 | 8 | | | 112 | | |
| 7 | | | 100 | | | |

TABLE VII-continued

| CD56, μg | Control | 37 | 39 | 40 | 41 | 42 |
|---|---|---|---|---|---|---|
| 6 | | | | 104 | | |
| 5 | | 82 | | | 88 | |
| 4 | | | | 87 | 75 | |
| 3 | | 65 | 75 | 79 | | 63 |
| 2 | | 50 | 51 | 69 | 65 | 55 |
| 1 | | 25 | | 43 | | 38 |
| 0.5 | | | | | | 29 |
| MFI Ratios, Fraction/Control | | | | | | |
| 8 | 1.0 | | | 14.0 | | |
| 7 | | | 12.4 | | | |
| 6 | | | | 13.0 | | |
| 5 | | 10.3 | | | 11.0 | |
| 4 | | | | 10.8 | 9.3 | |
| 3 | | 8.1 | 9.4 | 9.9 | | 7.8 |
| 2 | | 6.2 | 6.3 | 8.6 | 8.1 | 6.9 |
| 1 | | 3.1 | | 5.3 | | 4.8 |
| 0.5 | | | | | | 3.6 |

EXAMPLE 10
Flow Cytometric Analyses of Whole Blood with CD4-PE and CD4-5X-Amdex-PE Conjugates CD4 antibody conjugates were prepared to obtain an enhanced fluorescence standard with a tight distribution of intensities for lymphocytes. Titers of the control, CD4-PE at a concentration of 0.0625 mg/mL antibody, and the samples, CD4-5X-Amdex-PE from trial 4, starting with 3 μg antibody in the conjugate per tube, were mixed with 100 μL whole blood from a single normal blood donor for 30 minutes at room temperature. Concentrations of CD4 antibody in the conjugates were based on corrected $A_{280}$ values. After the mixing period all samples were submitted to a Q-PREP to lyse red blood cells and quench. The samples were further washed with 1 mL of 1×PBS by centrifugation for 5 minutes at 500 g, discarding the supernatant, and resuspending the cells in 1 mL 1×PBS. Mean channel PE fluorescence intensities relative to the control, obtained with a Coulter EPICS XL-MCL flow cytometer at the same instrument settings, are shown in Table VIII and given a maximum MFI ratio of 13.

TABLE VIII

| CD4, μg | Control | 36 | 37 | 38 | 39 | 40 | 41 | 42 | 43 |
|---|---|---|---|---|---|---|---|---|---|
| Mean Channel PE Fluorescence Intensities Fraction | | | | | | | | | |
| 3 | 44 | 443 | 499 | 513 | 478 | 471 | 393 | 357 | 298 |
| 2.5 | 42 | 420 | 489 | 507 | 467 | 482 | 392 | 371 | 323 |
| 2 | 42 | 393 | 451 | 463 | 425 | 448 | 396 | 362 | 319 |
| 1.5 | 42 | 352 | 379 | 384 | 412 | 425 | 376 | 355 | 321 |
| 1 | 41 | 281 | 296 | 293 | 343 | 331 | 319 | 327 | 316 |
| 0.5 | 40 | 78 | 220 | | 234 | 269 | 265 | 265 | 273 |
| MFI Ratios, Fraction/Control | | | | | | | | | |
| 3 | 1.0 | 11.0 | 12.4 | 12.7 | 11.9 | 11.7 | 9.7 | 8.8 | 7.4 |
| 2.5 | 1.0 | 10.4 | 12.1 | 12.6 | 11.6 | 12.0 | 9.7 | 9.2 | 8.0 |
| 2 | 1.0 | 9.7 | 11.2 | 11.5 | 10.5 | 11.1 | 9.8 | 9.0 | 7.9 |
| 1.5 | 1.0 | 8.7 | 9.4 | 9.5 | 10.2 | 10.5 | 9.3 | 8.8 | 8.0 |
| 1 | 1.0 | 7.0 | 7.3 | 7.3 | 8.5 | 8.2 | 7.9 | 8.1 | 7.8 |
| 0.5 | 1.0 | 1.9 | 5.5 | | 5.8 | 6.7 | 6.6 | 6.6 | 6.8 |

Figure 7A:
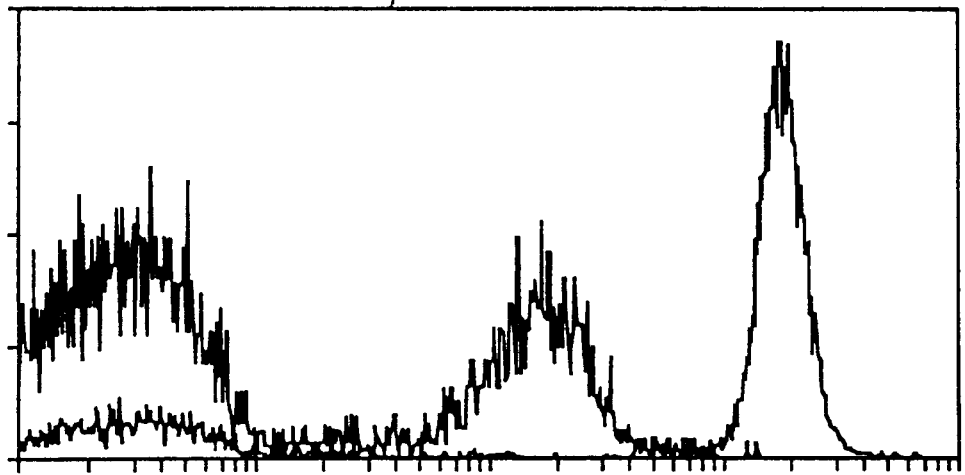
FIG. 7A is an overlay of two single color histograms showing the possible enumeration of mutually exclusive populations (CD56+ and CD4+) of white blood cells in whole blood with one direct fluorescent label-antibody conjugate (CD56-PE) and another enhanced, aminodextran-crosslinked fluorescent label-antibody conjugate of the same fluorescent label (CD4-5X-Amdex-PE) run with 488.0 nm Ar+ laser excitation on a Coulter XL flow cytometer.
Figure 7B:
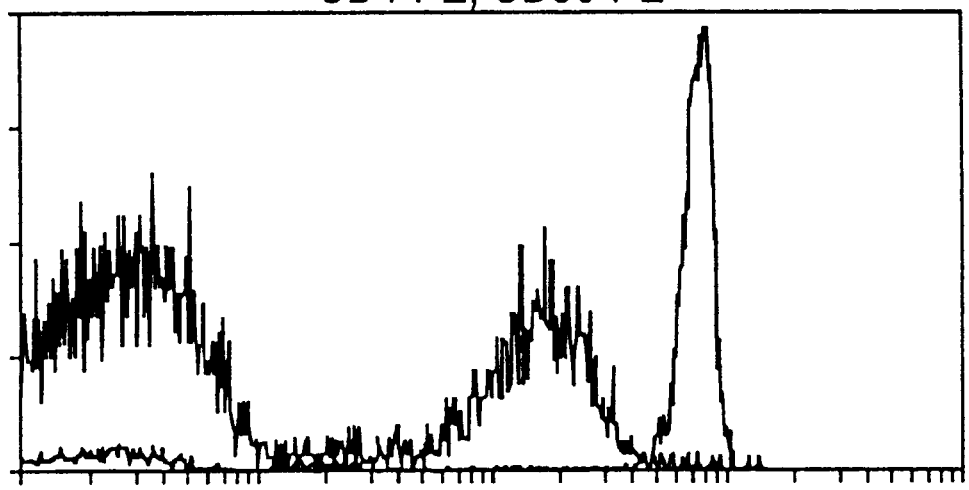
FIG. 7B is a similar set of histograms as for FIG. 7A, but obtained by using the pair of direct conjugates, CD56-PE and CD4-PE, showing some overlap between the CD56+ and CD4+ distributions.
Figure 8A:
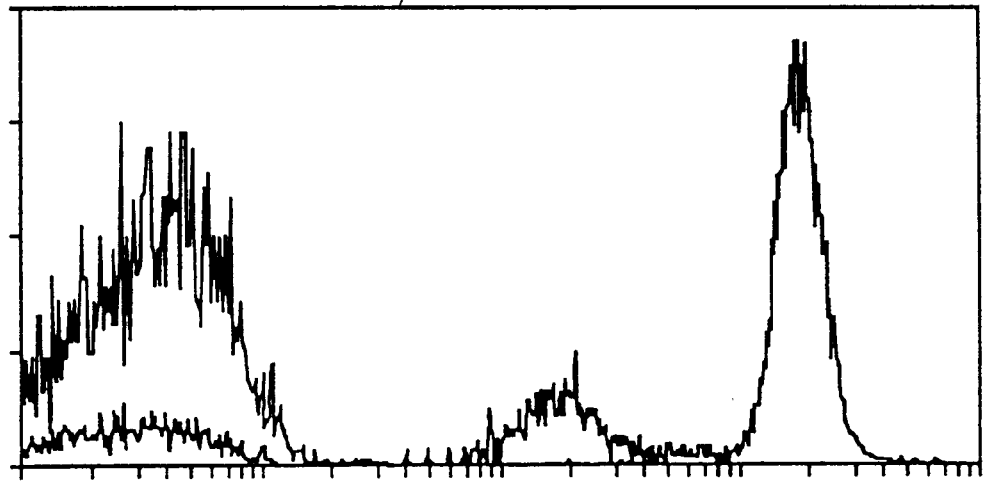
FIG. 8A is a histogram similar to that of FIG. 7A for pairs of markers, CD 19-PE and CD4-5X-Amdex-PE.
Figure 8B:
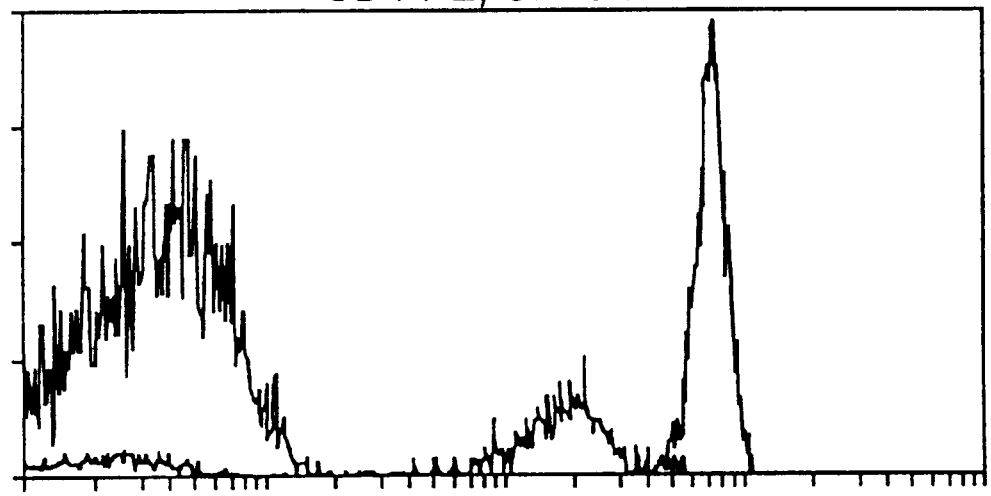
FIG. 8B is a histogram similar to that of FIG. 8A for two directly conjugated pairs of markers, CD19-PE and CD4-PE.
Figure 9A:
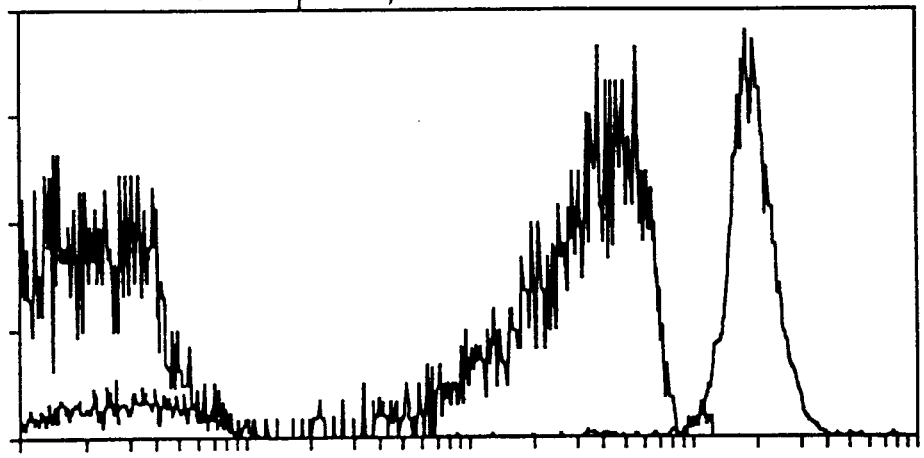
FIG. 9A is a histogram similar to that of FIG. 8A for pairs of markers, CD8αβ-PE and CD4-5X-Amdex-PE.
Figure 9B:
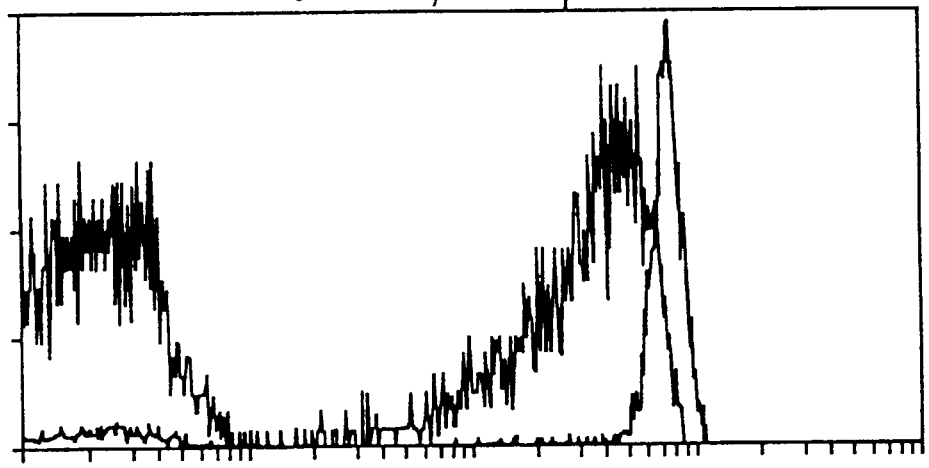
FIG. 9B is a histogram similar to that of FIG. 9A for two directly conjugated pairs of markers, CD4-PE and CD8αβ-PE.
Figure 10B:
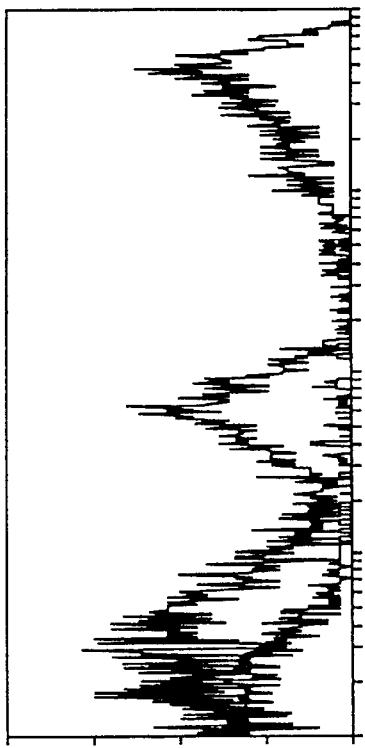
FIG. 10B is a histogram similar to that of FIG. 10A, but obtained with a different titer of the CD8αβ-5X-Amdex-PC5 marker to show optimum separation between the position of the positive and negative count versus intensity distributions.
Figure 10A:
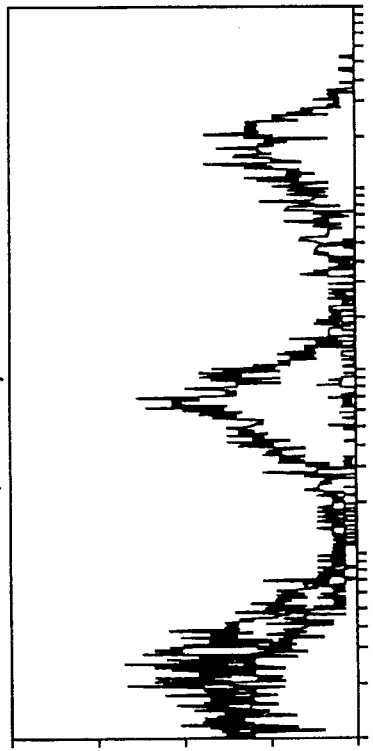
FIG. 10A is a histogram similar to that of FIG. 9A using markers CD56-PC5 and CD8αβ-5X-Amdex-PC5.
Figure 10C:
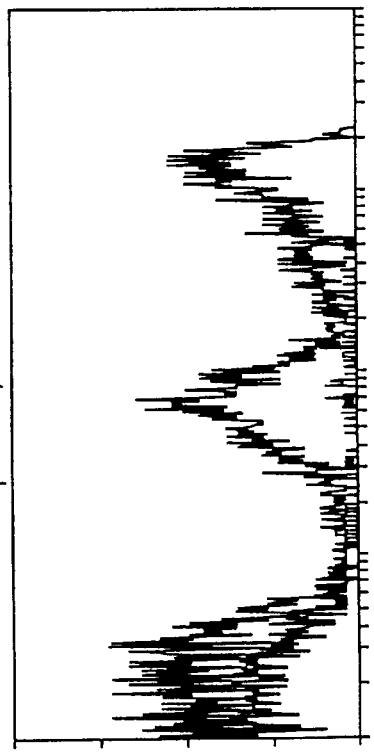
FIG. 10C is a histogram similar to that of FIG. 9A using markers CD8αβ-PC5 and CD56-PC5.
Figure 12A:
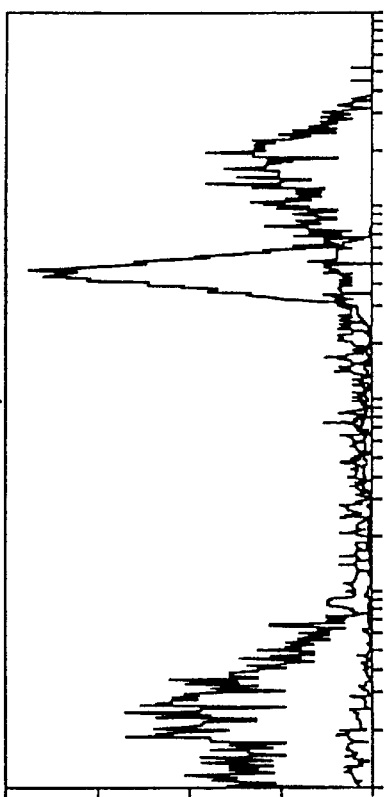
FIG. 12A is a histogram similar to that of FIG. 10A using markers CD4-PC5 and CD8αβ-5X-Amdex-PC5.
Figure 12B:
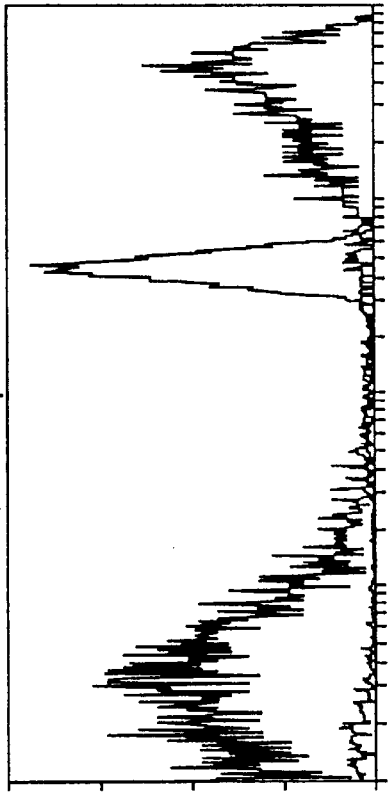
FIG. 12B is a histogram similar to that of FIG. 12A, but obtained with a different titer of the CD8αβ-5X-Amdex-PC5 marker to show optimum separation between the position of the positive and negative count versus intensity distributions.
Figure 12C:
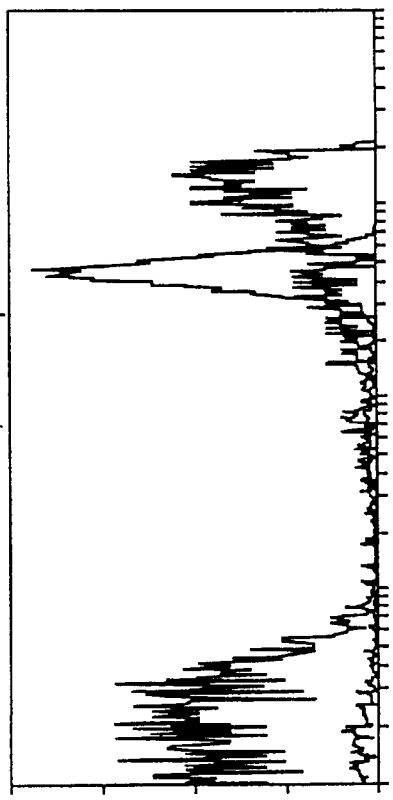
FIG. 12C is a histogram similar to that of FIG. 11C using markers CD4-PC5 and CD8αβ-PC5.

EXAMPLE 11
Use of Dual Intensity, Same Color Markers in Flow Cytometric Analyses A. Overlayed Single Histograms of Pairs of Same Color Fluorescent Markers—Direct versus Enhanced Label The ability to enumerate mutually exclusive populations of white blood cells in whole blood with one direct fluorescent label-antibody conjugate and another enhanced, aminodextran-crosslinked fluorescent label-antibody conjugate of the same fluorescent label, is demonstrated in the following examples run with 488.0 nm Ar⁺ laser excitation on a Coulter EPICS XL-MCL flow cytometer. The first pair of markers is CD56-PE and CD4-5X-Amdex-PE, used to obtain the single color histograms that were overlayed and are shown in FIG. 7A. The amplified and narrowly-distributed CD4+ population in the fourth decade of the fluorescence intensity scale is well-separated from the intrinsically weak and broader CD56+ population bordering the second and third decades of the intensity scale. Also, note that the background fluorescence from the CD4+ cells does not interfere with the signal from the CD56+ cells. A similar set of histograms obtained by using the pair of direct conjugates, CD56-PE and CD4-PE, is displayed in FIG. 7B and shows some overlap between the CD56+ and CD4+ distributions.

Similar overlayed histograms are shown in FIGS. 8A through 9B for pairs of markers, CD19-PE and CD4-5X-Amdex-PE, CD8αβ-PE and CD4-5X-Amdex-PE, and in FIGS. 10A through 12C for CD56-PC5 and CD8αβ-5X-Amdex-PC5, CD19-PC5 and CD8αβ-5X-Amdex-PC5, CD4-PC5 and CD8αβ-5X-Amdex-PC5. FIGS. 10B, 11B and 12B show histograms obtained with a different titer of the CD8αβ-5X-Amdex-PC5 marker to show optimum separation between the peaks in the labeled cell count versus fluorescence intensity distributions.

Further combinations of CD4-PE, CD19-PE, or CD8αβ-PE marker with CD56-5X-Amdex-PE marker did not yield favorable separation due to the intrinsically broad intensity distributions for CD56 positive and negative populations of cells, and generally lower numbers of CD56 receptors per cell compared to CD4+ or CD8αβ+ receptors per cell. Thus, when a higher intensity marker is used with an enhanced CD56 marker, the overlap between CD56 and CD4 or CD8αβ intensity distributions is even greater.

Figure 13A:
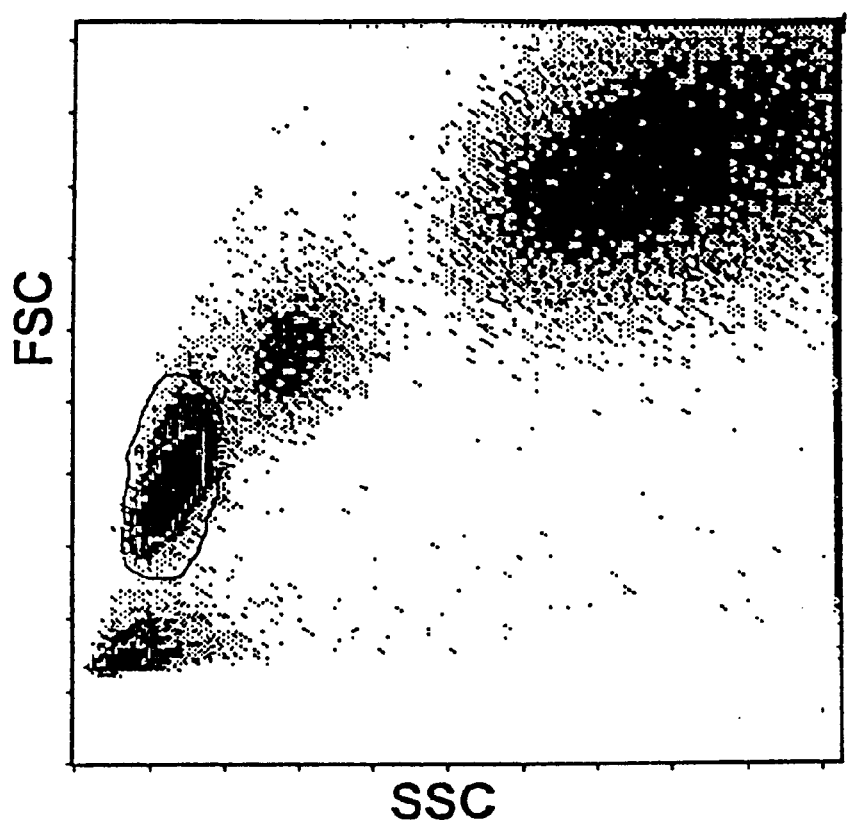
FIG. 13A is the FS versus SS histogram from two direct fluorochrome-antibody conjugates, CD56-PE and CD19-PC5, and two aminodextran crosslinked conjugates, CD4-5X-Amdex-PE and CD8αβ-5X-Amdex-PC5, used simultaneously to analyze for CD56+(NK cells), CD4+(T4 cells), CD19+(B cells), and CD8αβ+(T8 cells) in the scatter-gated lymphocyte population of white blood cells of a normal blood donor run with 488.0 nm Ar+ laser excitation on the Coulter XL flow cytometer.
Figure 13B:
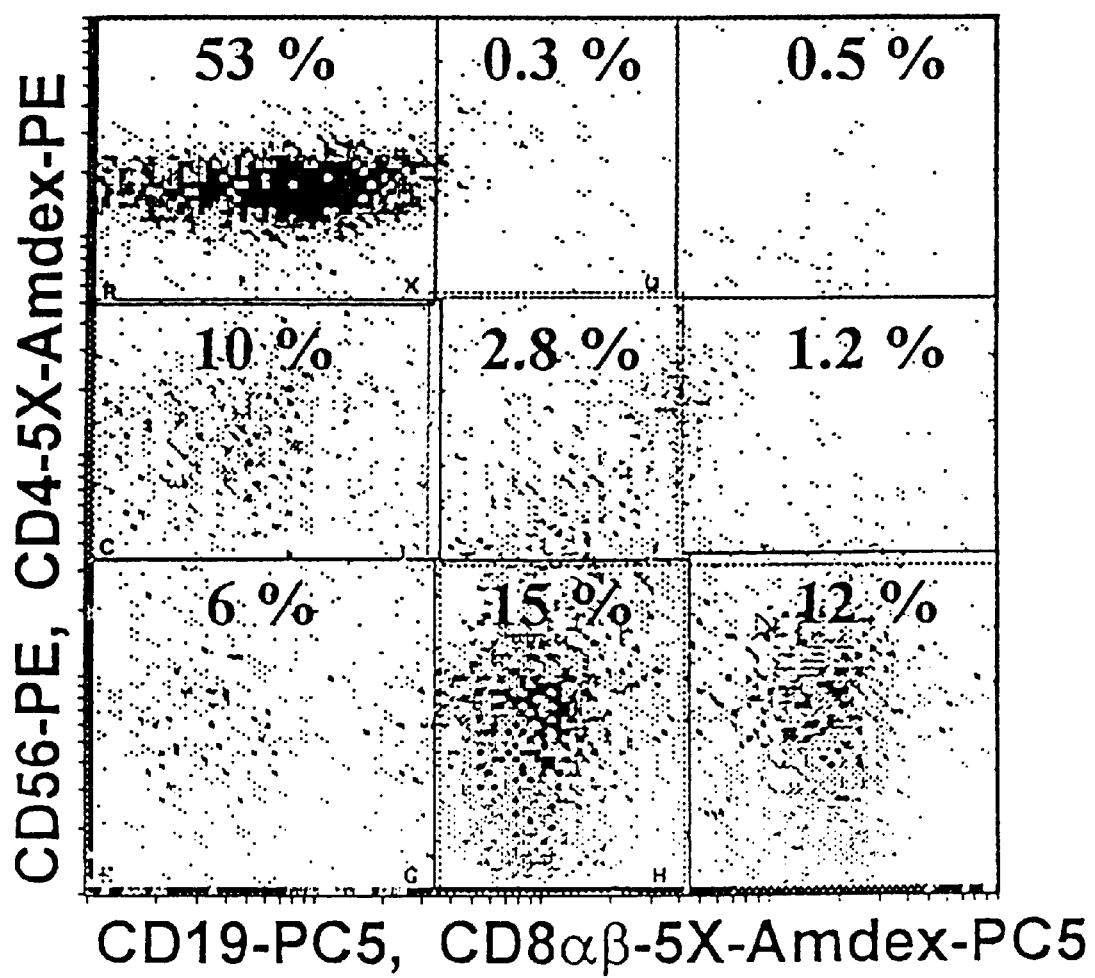
FIG. 13B is a dual color PE(CD56/CD4-5X-Amdex) versus PC5(CD19/CD8αβ-5X-Amdex) fluorescence intensity histogram of the experiment of FIG. 13A.
Figure 14:
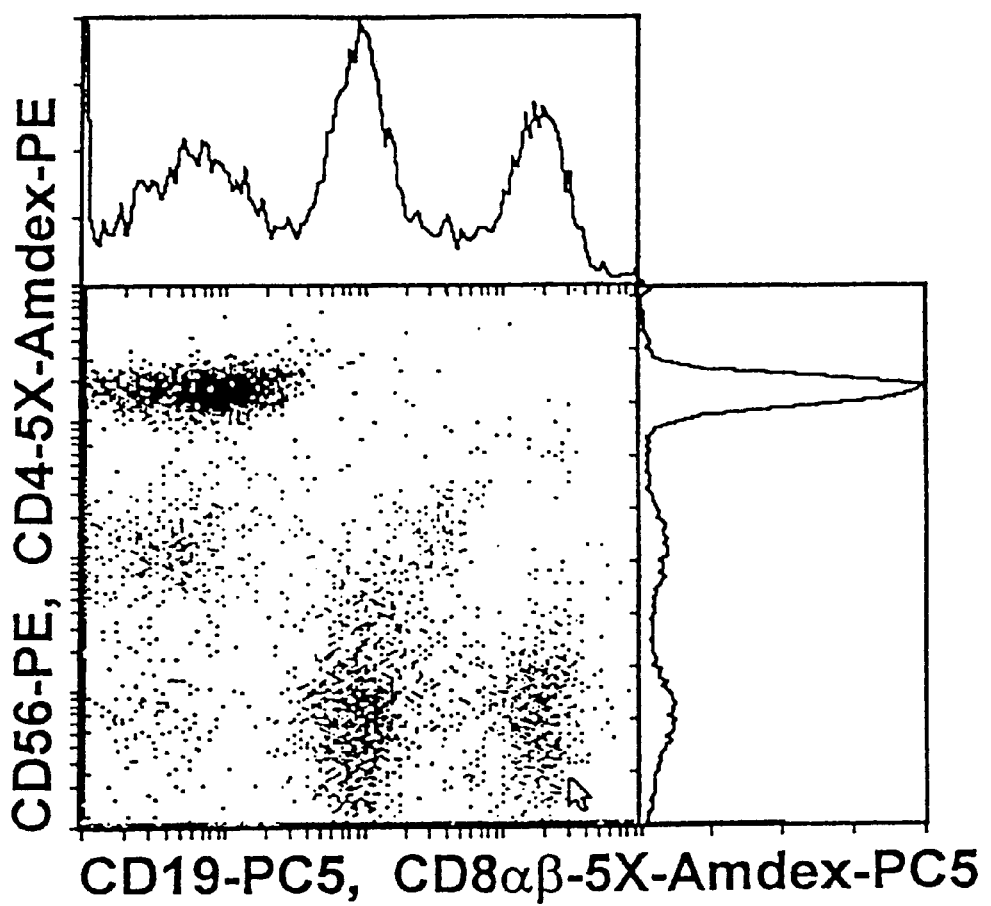
FIG. 14 is projection display of the dual parameter display of PE vs. PC as a single color cell count versus PC5(CD19/CD8αβ-5X-Amdex) fluorescence intensity histogram and the single color count versus PE (CD56/CD4-5X-Amdex) fluorescence intensity histogram. The two single color histograms which form the upper histogram and right histogram of this figure, each contain one direct fluorochrome-antibody marker and an enhanced intensity, aminodextran-crosslinked, marker of the same color. These show good separation of the enhanced marker in the fourth decade of the fluorescence intensity scale from the usual marker with maximum mean channel fluorescence intensity in the second or third decade.
Figure 15A:
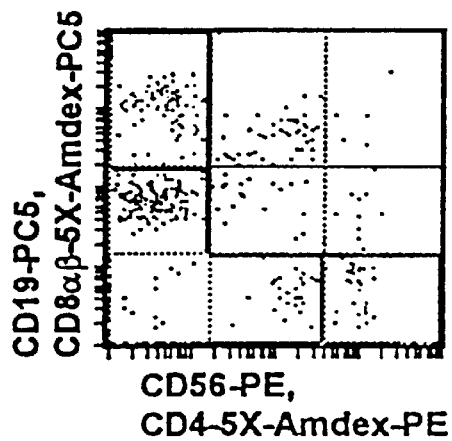
FIGS. 15A–15D represent the set of dual parameter histograms from a six marker, four color, single stain experiment.
Figure 15B:
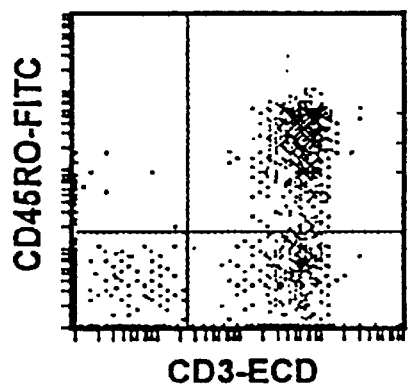
Figure 15C:
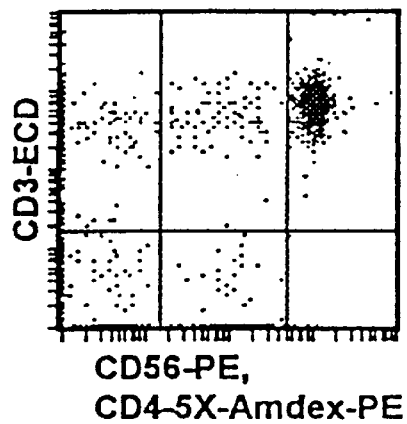
Figure 15D:
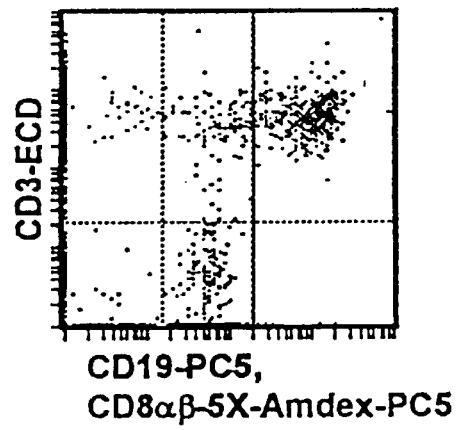

B. Use of Four Markers, Dual Color, with Single Laser Excitation Line in Flow Cytomyetric Analysis Two direct fluorochrome-antibody conjugates, CD56-PE and CD19-PC5, and two aminodextran crosslinked conjugates, CD4-5X-Amdex-PE and CD8αβ-5X-Amdex-PC5, were used simultaneously to analyze for CD56+ (NK cells), CD4+(T4 cells), CD19+ (B cells), and CD8αβ+ (T8 cells) in the scatter-gated lymphocyte population of white blood cells of a normal blood donor run with 488.0 nm Ar+ laser excitation on the Coulter EPICS XL-MCL flow cytometer. The FS versus SS and dual color PE (CD56/CD4-5X-Amdex) versus PC5 (CD19/CD8αβ-5X-Amdex) fluorescence intensity histograms are shown in FIGS. 13A and 13B. Also cell count versus PC5 (CD19/CD8αβ-5X-Amdex) fluorescence intensity histograms are shown in the projection display in FIG. 14. The two single color projection histograms (in the upper and right hand side of this figure), each containing one direct fluorochrome-antibody marker and an enhanced intensity, aminodextran-crosslinked, marker of the same color, show good separation of the enhanced marker in the fourth decade of the fluorescence intensity scale from the usual marker with maximum mean channel fluorescence intensity in the second or third decade. As labeled on the histograms of FIG. 13B, the positive CD56, CD4, CD19, and CD8αβ cell populations account for 90% of events displayed on the dual color histogram.

C. Use of Six Markers, Four Color with Single Laser Excitation Line in Flow Cytometric Analysis Two additional color markers, CD3-ECD and CD45RO-FITC were mixed with whole blood already containing the dual color, four markers CD56-PE/CD4-5X-Amdex-PE and CD19-PC5/CD8αβ-5X-Amdex-PC5. The Q-PREPed and washed samples were run with 488.0 nm Ar+ laser excitation on the Coulter EPICS XL-MCL flow cytometer; then, the sets of histograms in FIGS. 15A through 15D, demonstrating resolution of 25 different targeted white blood cell populations were obtained. Furthermore, seven marker, four color analysis could be obtained with a single laser excitation line by adding the pair of markers, CD16-ECD and CD3-5X-Amdex-ECD, instead of CD3-ECD in the six marker experiment.

All publications cited in this specification are indicative of the level of skill of those in the art to which this application pertains. The disclosure of parent U.S. patent application Ser. No. 08/857,941 is incorporated by reference. Each publication is individually incorporated herein by reference in the location where it is cited.

While the invention has been described with reference to a particularly preferred embodiment, it will be appreciated that numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A ligand aminodextran-tandem dye conjugate, which conjugate contains two to twenty phycobiliproteins per aminodextran molecule, wherein said aminodextran has a degree of substitution with 1,3-diaminopropane of 1/40 to 1/7, said 1,3-diaminopropane coupled with aldehyde functional groups on oxidized dextran sugar rings.

2. The conjugate according to claim 1 wherein said tandem dye is selected from the group consisting of phycoerythro-cyanin 5.1, phycoerythrin-cyanin 7.1, phycoerythrin-texas red, allophycocyanin 5.1, and allophycocyanin 7.1.

3. The conjugate according to claim 1, wherein the aminodextran is 5X-aminodextran.

4. The conjugate according to claim 1, wherein the aminodextran is 1X-aminodextran.

5. The conjugate according to claim 1, wherein said ligand is an antibody or functional fragment thereof capable of binding to a cell surface receptor on a white blood cell population.

* * * * *